United States Patent
Wang et al.

(10) Patent No.: US 10,970,887 B2
(45) Date of Patent: Apr. 6, 2021

(54) TOMOGRAPHIC IMAGE RECONSTRUCTION VIA MACHINE LEARNING

(71) Applicant: RENSSELAER POLYTECHNIC INSTITUTE, Troy, NY (US)

(72) Inventors: Ge Wang, Loudonville, NY (US); Wenxiang Cong, Albany, NY (US); Qingsong Yang, Sunnyvale, CA (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/312,704

(22) PCT Filed: Jun. 26, 2017

(86) PCT No.: PCT/US2017/039274
§ 371 (c)(1),
(2) Date: Dec. 21, 2018

(87) PCT Pub. No.: WO2017/223560
PCT Pub. Date: Dec. 28, 2017

(65) Prior Publication Data
US 2019/0325621 A1   Oct. 24, 2019

Related U.S. Application Data

(60) Provisional application No. 62/354,319, filed on Jun. 24, 2016.

(51) Int. Cl.
*G06T 11/00* (2006.01)
*G06N 20/00* (2019.01)
*G06N 3/08* (2006.01)

(52) U.S. Cl.
CPC .............. *G06T 11/008* (2013.01); *G06N 3/08* (2013.01); *G06N 20/00* (2019.01); *G06T 11/006* (2013.01);
(Continued)

(58) Field of Classification Search
CPC . G06T 11/008; G06T 11/006; G06T 2210/41; G06T 2211/421; G06T 2211/424; G06N 20/00; G06N 3/08
See application file for complete search history.

(56) References Cited

U.S. PATENT DOCUMENTS 6,577,700 B1   6/2003   Fan et al.
9,324,022 B2   4/2016   Williams, Jr. et al.
(Continued)

OTHER PUBLICATIONS

International Search Report of the International Searching Authority, International Application No. PCT/US2017/039274 dated Sep. 29, 2017.

*Primary Examiner* — Khai M Nguyen
(74) *Attorney, Agent, or Firm* — Murtha Cullina LLP; Anthony P. Gangemi

(57) ABSTRACT

Tomographic/tomosynthetic image reconstruction systems and methods in the framework of machine learning, such as deep learning, are provided. A machine learning algorithm can be used to obtain an improved tomographic image from raw data, processed data, or a preliminarily reconstructed intermediate image for biomedical imaging or any other imaging purpose. In certain cases, a single, conventional, non-deep-learning algorithm can be used on raw imaging data to obtain an initial image, and then a deep learning algorithm can be used on the initial image to obtain a final reconstructed image. All machine learning methods and systems for tomographic image reconstruction are covered, except for use of a single shallow network (three layers or less) for image reconstruction.

20 Claims, 14 Drawing Sheets

(52) U.S. Cl.
 CPC ..... *G06T 2210/41* (2013.01); *G06T 2211/421* (2013.01); *G06T 2211/424* (2013.01)

(56) References Cited

U.S. PATENT DOCUMENTS

| | | | |
|---|---|---|---|
| 2014/0363067 A1 | 12/2014 | Stayman et al. | |
| 2015/0201895 A1* | 7/2015 | Suzuki | A61B 6/5211 |
| | | | 382/131 |
| 2016/0093048 A1* | 3/2016 | Cheng | G06K 9/6289 |
| | | | 382/131 |
| 2017/0294034 A1* | 10/2017 | Zhou | G06T 11/008 |
| 2017/0362585 A1* | 12/2017 | Wang | G06N 3/08 |

* cited by examiner

TOMOGRAPHIC IMAGE RECONSTRUCTION VIA MACHINE LEARNING

CROSS REFERENCE TO RELATED APPLICATION

This application is a national stage filing of International Patent Application No. PCT/US2017/039274, filed Jun. 26, 2017, which claims the benefit of U.S. Provisional Patent Application No. 62/354,319, filed Jun. 24, 2016, which are incorporated herein by reference in their entireties.

BACKGROUND

Medical imaging includes two major components: (1) image formation and reconstruction, from data to images; and (2) image processing and analysis, from images to images (e.g., de-noising and artifact reduction, among other tasks) and from images to features (e.g., recognition, among other tasks). While many methods exist for image processing and analysis, there is a relative dearth when it comes to image formation and reconstruction, and existing systems and methods in this area still exhibit many drawbacks.

BRIEF SUMMARY

Embodiments of the subject invention provide image reconstruction systems and methods using deep learning, which can help address drawbacks of related art image formation and/or reconstruction methods. A deep learning algorithm (e.g., performed by a deep neural network) can be used to obtain a reconstructed image from raw data (e.g., features) obtained with medical imaging (e.g., CT, MRI, X-ray). In certain cases, a conventional (i.e., non-deep-learning) reconstruction algorithm can be used on the raw imaging data to obtain an initial image, and then a deep learning algorithm (e.g., performed by a deep neural network) can be used on the initial image to obtain a reconstructed image. Also, though not necessary, a training set and/or set of final images can be provided to a deep network to train the network for the deep learning step (e.g., versions of what a plurality of final images should look like are provided first, before the actual image reconstruction, and the trained deep network can provide a more accurate final reconstructed image).

In an embodiment, a method of reconstructing an image from tomographic data can comprises performing at least one algorithm on the tomographic data to obtain a reconstructed image, the at least one algorithm comprising a deep learning algorithm.

BRIEF DESCRIPTION OF DRAWINGS

FIG. 12A shows a normal dose CT image; FIG. 12B shows a quarter dose image of the same abdomen; FIG. 12C shows the result of image reconstruction using a CNN network with mean squared error (MSE) loss; and FIG. 12D shows the result of image reconstruction result using a Wasserstein GAN (WGAN) framework with perceptual loss.

FIG. 13A show the ground truth mono-energetic sinogram; and FIG. 13B shows the mono-energetic sinograms output by the CNN.

FIG. 15A is the original nodule image; FIG. 15B shows the image of FIG. 15A after random rotation;

FIG. 15C is after random flip; FIG. 15D is after random shift; FIG. 15E is after random zoom; and FIG. 15F is after random noise.

FIG. 23A shows an original image; FIG. 23B shows the image of FIG. 23A reconstructed by deep learning interpolation of a metal trace region; and FIG. 23C shows the image of FIG. 23A reconstructed by linear interpolation of a metal trace region.

FIG. 23D shows the difference between the reconstruction of FIG. 23B (deep learning) and the original image of FIG. 23A; and FIG. 23E shows the difference between the reconstruction of FIG. 23C (linear interpolation) and the original image of FIG. 23A. The deep learning reconstruction leads to clear improvement of banding and streaking artifacts, corresponding to a root mean square (RMS) error improvement of 37%. The remaining artifacts in the result obtained with the deep learning were predominantly of a high-frequency nature, which may be due to the relatively small number of layers and neurons in the network used.

DETAILED DESCRIPTION

Embodiments of the subject invention provide image reconstruction systems and methods using deep learning or machine learning. A deep learning algorithm (e.g., performed by a deep neural network) can be used to obtain a reconstructed image from raw data (e.g., features) obtained with medical imaging (e.g., CT, MRI, X-ray). In a specific embodiment, a conventional (i.e., non-deep-learning) reconstruction algorithm can be used on the raw imaging data to obtain an initial reconstructed image, which would contain articfacts due to low dose, physical model approximation, and/or beam-hardening. Then, a deep learning algorithm (e.g., performed by a deep neural network) can be used on the initial reconstructed image to obtain a high-quality reconstructed image. In many embodiments, a training data set and/or set of final images can be provided to a deep network to train the network for the deep learning step so that a function model is established to describe the relation between low-quality input images and high-quality output images.

Figure 1:
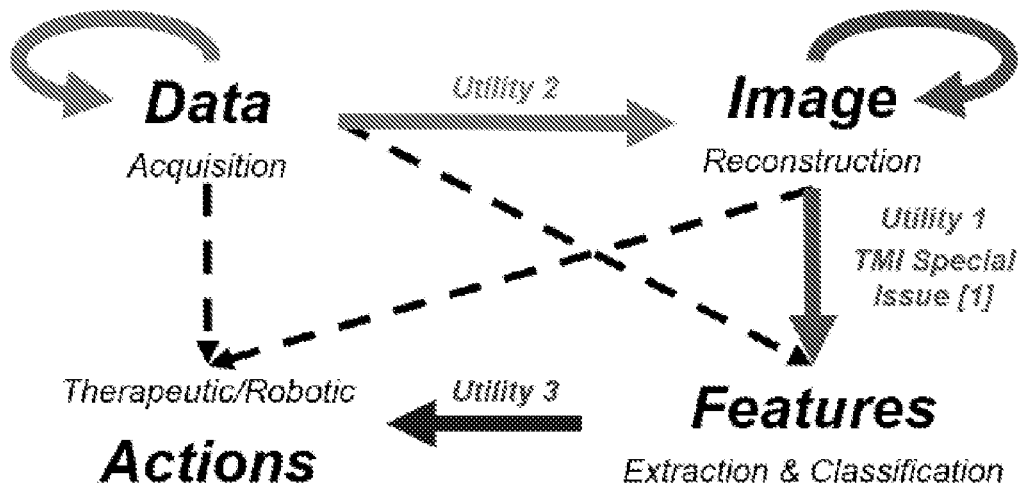
FIG. 1 shows a schematic representation of deep imaging.

The combination of medical imaging, big data, deep learning, and high-performance computing promises to empower not only image analysis but also image reconstruction. FIG. 1 shows a schematic of deep imaging, a full fusion of medical imaging and deep learning. Further advantages of imaging using deep learning are discussed in [154], which is incorporated by reference herein in its entirety. Also, certain aspects of some of the examples disclosed herein are discussed in references [107], [150], [151], [152], and [153], all of which are incorporated by reference herein in their entireties.

Figure 2:
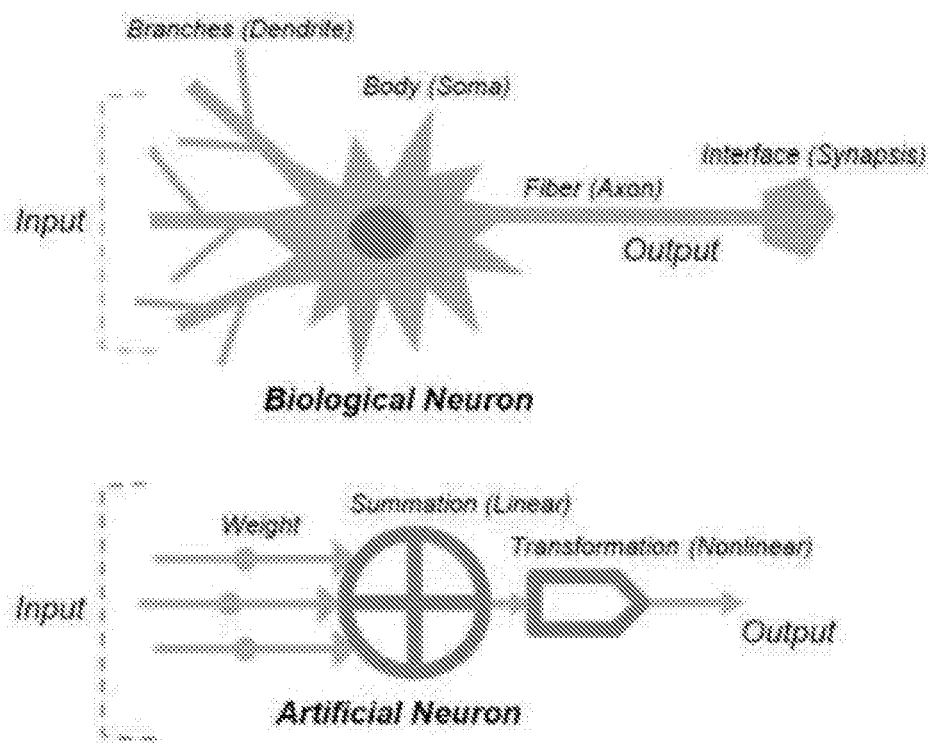
FIG. 2 shows a schematic representation of a biological neuron and an artificial neuron.

As the center of the nervous system, the human brain contains many billions of neurons, each of which includes a body (soma), branching thin structures from the body (dendrites), and a nerve fiber (axon) reaching out. Each neuron is connected by interfaces (synapses) to thousands of neighbors, and signals are sent from axon to dendrite as electrical pulses (action potentials). Neuroscience views the brain as a biological computer whose architecture is a complicated biological neural network, where the human intelligence is embedded. In an engineering sense, the neuron is an electrical signal processing unit. Once a neuron is excited, voltages are maintained across membranes by ion pumps to generate ion concentration differences through ion channels in the membrane. If the voltage is sufficiently changed, an action potential is triggered to travel along the axon through a synaptic connection to another neuron. The dynamics of the whole neural network is far from being fully understood. Inspired by the biological neural network, artificial neurons can be used as elements of an artificial neural network. This elemental model linearly combines data at input ports like dendrites, and non-linearly transforms the weighted sum into the output port like the axon. FIG. 2 shows a schematic view of a biological neuron and an artificial neuron.

Figure 3:
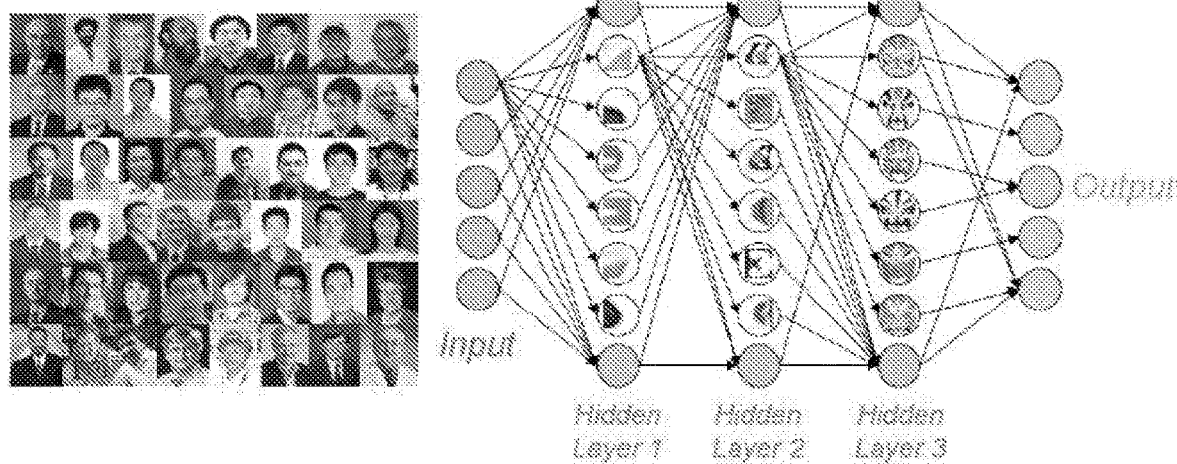
FIG. 3 shows a schematic representation of a deep network for feature extraction and classification through non-linear multi-resolution analysis.

Deep neural networks have had success in computer vision, speech recognition, and language processing. Consider a neural network that works for face recognition as an example, as shown in FIG. 3. Referring to FIG. 3, there are many layers of neurons with inter-layer connections in a deep network. Data are fed into the input layer of the network, and weights associated with the neurons are typically obtained in a pre-training and fine-tuning process or a hybrid training process with a large set of unlabeled and labeled images. Results are obtained from the output layer of the network, and other layers are hidden from direct access. Each layer uses features from the previous one to form more advanced features. At earlier layers, more local features are analyzed such as edges, corners, and facial motifs. At later layers, more global features are synthesized to match face templates. Thanks to innovative algorithmic ingredients that have been developed, this deep learning mechanism has been made effective and efficient for feature extraction from images, and has demonstrated surprising capabilities. A deep network is fundamentally different from many other multi-resolution analysis schemes and optimization methods. A distinguished niche of deep networks is the nonlinear learning and optimization ability for nonconvex problems of huge dimensionality that used to challenge machine intelligence.

While FIG. 3 illustrates the process from images to features, it would be advantageous to go from projection/tomographic data to reconstructed images. The raw data collected for tomographic reconstruction can be considered as features of images, which are oftentimes approximated as linearly combined image voxel values, and more accurately modeled as nonlinear functions of the image parameters. Thus, image reconstruction is from raw data (features measured with tomographic scanning) to images, an inverse of the recognition workflow from images to features in FIG. 3. Embodiments of the subject invention can include image reconstruction from raw data to images using deep learning.

A classic mathematical finding of artificial neural networks is the so-called universal approximation theorem that, with a reasonable activation function, a feed-forward network containing only a single hidden layer may closely approximate an arbitrary continuous function on a compact subset when parameters are optimally specified. Then, the assumption on the activation function was greatly relaxed, leading to a statement that "it is not the specific choice of the activation function, but rather the multilayer feedforward architecture itself which gives neural networks the potential of being universal learning machines". Although a single hidden layer neural network can approximate any function, it is highly inefficient to handle big data since the number of neurons would grow exponentially. With deep neural networks, depth and width can be combined to more efficiently represent functions to high precision, and also more powerfully perform multi-scale analysis, quite like wavelet analysis but in a nonlinear manner.

If the process from images to features is considered as a forward function, the counterpart from features to images can be thought of as an inverse function. Just like such a forward function has been successfully implemented in the deep network for many applications, so should be the inverse function for various tomographic modalities, both of which are guaranteed by the intrinsic potential of the deep network for a general functional representation, be it forward or inverse. Because the forward neural network is deep (many layers from an image to features), it is natural to expect that the inverse neural network should be also deep (many layers from raw data to an image). Despite special cases in which relatively shallow networks may work well, the neural network should be generally deep when the problem is complicated and of high dimensionality so that the aforementioned representation efficiency and multi-resolution analysis can be achieved through optimization of depth and width to combat the curse of dimensionality.

Figure 5:
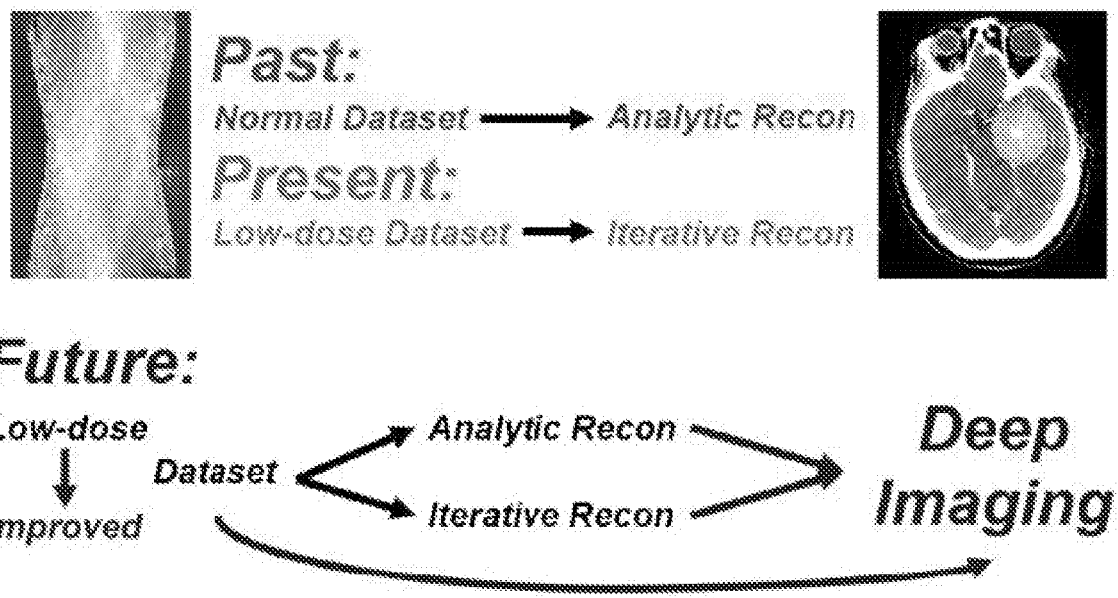
FIG. 5 shows a schematic representation of the past, present, and future of computed tomography (CT) image reconstruction.

Consider computed tomography (CT) as a non-limiting example. It can be imagined that many CT reconstruction algorithms can be covered in the deep imaging framework, as suggested in FIG. 5. In the past, image reconstruction was focused on analytic reconstruction, and analytic reconstruction algorithms are present even in the intricate helical cone-beam geometry, which implicitly assume that data are accurate. With the increasing use of CT scans and associated public concerns on radiation safety, iterative reconstruction algorithms became gradually more popular. Many analytic and iterative algorithms should be able to be upgraded to deep imaging algorithms to deliver superior diagnostic performance.

When a projection dataset is complete, an analytic reconstruction would bring basically full information content from the projection domain to the image space even if data are noisy. If a dataset is truncated, distorted, or otherwise severely compromised (for example, limited angle, few-view, local reconstruction, metal artifact reduction, beam-hardening correction, scatter suppression, and motion restoration problems), a suitable iterative algorithm can be used to reconstruct an initial image. It is the image domain where a system of an embodiment of the subject invention can be good at de-noising, de-streaking, de-blurring, and interpretation. In other words, existing image reconstruction algorithms can be utilized to generate initial images, and then deep networks can be used to do more intelligent work based on initial images. This two-stage approach is advantageous as an initial strategy for three reasons. First, all the well-established tomographic algorithms are still utilized. Second, domain-specific big data can be fully incorporated as unprecedented prior knowledge for training a neural network. Third, the trained deep neural network(s) can easily produce a high-quality image from an input image. With this approach, the neural network is naturally a nonlinear mapping because medical image processing and analysis can be effectively performed by a deep network. Similarly, a sinogram can be viewed as an image, and a deep learning algorithm can be used to improve a low-dose or otherwise compromised sinogram. This transform from a poor sinogram to an improved sinogram is another type of image processing task, and can be performed via deep learning.

Then, a better image can be reconstructed from the improved sinogram. As mathematically discussed above in terms of forward and inverse functions, both analytic and iterative reconstruction algorithms can be implemented or approximated with deep networks. This viewpoint can also be argued from an algorithmic perspective. Indeed, either the filtered back-projection (FBP) or simultaneous algebraic reconstruction technique (SART) can be easily formulated in the form of parallel layered structures (for iterative reconstruction, the larger the number of iterations, the deeper the network will be). Then, a straightforward method for deep imaging, according to an embodiment, can be just from raw data to an initial image through a neural network modeled after a traditional reconstruction scheme, and then from the initial image to a final high-quality image through a refinement deep network. This streamlined procedure can be extended to unify raw data pre-processing, image reconstruction, image processing, and image analysis, leading to even deeper network solutions. In the cases of missing or distorted data, the deep network can make a best link from measured data to reconstructed images in the sense of the best nonlinear fit in terms of big data.

The above considerations apply to other medical imaging modalities because all these biomedical imaging problems are associated with similar formulations in the general category of inverse problems. To the first order approximation, a majority of medical imaging algorithms have Fourier or wavelet transform related versions, and could be helped by some common deep networks. For nonlinear imaging models, deep imaging should be an even better strategy, given the nonlinear nature of deep networks. While the multimodality imaging trend promotes a system-level integration, deep imaging might be a unified information theoretic framework or a meta-solution to support either individual or hybrid scanners.

The imaging algorithmic unification is consistent with the successes in the artificial intelligence field in which deep learning procedures follow very similar steps despite the problems appearing rather different, such as chess playing, electronic gaming, face identification, and speech recognition. Just as a unified theory is preferred in the physical sciences, a unified medical imaging methodology would have advantages so that important computational elements for network training and other tasks could be shared by all the modalities, and the utilization of inter-modality synergy could be facilitated since all the computational flows are in the same hierarchy consisting of building blocks that are artificial neurons and also hopefully standard artificial neural circuits.

A key prerequisite for deep imaging is a training set that spans the space of all relevant cases. Otherwise, even an optimized deep network topology could be disappointing in real world applications. Also, it remains an open issue which reconstruction schemes would be better—classic analytic or iterative algorithms, deep networks, hybrid configurations, or unified frameworks. The answer can be application-dependent. For a clean dataset, the conventional method works well. For a challenging dataset, the deep network can be used. In any case, deep learning can be (theoretically and/or practically) relevant to medical imaging.

Figure 4:
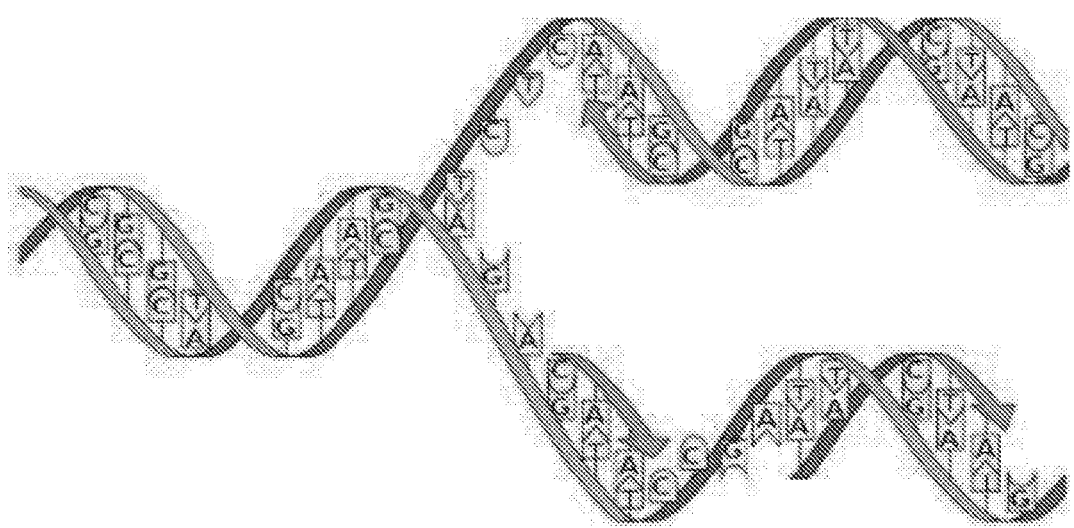
FIG. 4 shows a schematic visualization of inner product as a double helix.

From a perspective of theoretical physics, the concept of the renormalization group (RG, related to conformal invariance by which a system behaves the same way at different scales) has been utilized for understanding the performance of deep learning. Deep learning may be an RG-like scheme to learn features from data. Each neuron is governed by an activation function which takes data in the form of an inner product, instead of input data directly. The inner product is computed as a sum of many products of paired data, which can be visualized as a double helix as shown in FIG. 4, in which the paired results between the double helix are lumped together. In other words, it is suggested that the inner product is the fundamental construct for deep learning, and in this sense it serves as "DNA" for data analysis. This view is mathematically meaningful because most mathematical transforms including matrix multiplications are calculated via inner products. The inner products are nothing but projections onto appropriate bases of the involved space. Cross- and auto-correlations are inner products, common for feature detection and filtration. Projections and back-projections are inner products as well. Certainly, the inner product operation is linear, and methods should not be limited to linear spaces. Then, the nonlinear trick comes as an activation function (see also FIG. 2).

In a deep network, the alternating linear and nonlinear processing steps seem to hint that the simplest linear computational elements (inner products) and simplest nonlinear computational elements (monotonic activation functions) can be organized to perform highly complicated computational tasks. Hence, the principle of simplicity applies not only to physical sciences but also to information/intelligence sciences, and the multi-resolution phenomena seems merely a reflection of this principle. When inner products are performed, linear elements of machine intelligence are realized; when the activation steps (in a general sense, other effects are included such as pooling and dropout) are followed, the non-linear nature of the problem is addressed; so on and so forth, from bottom up (feed forward) and from top down (back propagation).

Most existing analytic and iterative algorithms were designed for linear imaging problems. If the linear system model is accurate, at the first look, there appears no need to trade analytic and statistical insight for nonlinear processing advantages of deep networks through intensive tedious training. Nevertheless, even in that case, deep imaging is conceptually simple, universally applicable, and the best platform to fully utilize domain specific knowledge extracted from big data. Such comprehensive contextual prior knowledge cannot be utilized by iterative likelihood/Bayesian algorithms, which are nonlinear but limited to compensation for statistical fluctuation. Additionally, with the principle of simplicity, deep imaging is preferred, using the analogy of digital over analog computers.

Deep learning has achieved impressive successes in practice but a decent theory remains missing. Open issues include why ConvNet works well, how many layers, neurons, and free parameters are needed, and questions about local minima, structured predictions, short-term/working/episodic memories, and better learning methods. Also, slightly different images could be put into distinct classes, and random images could be accepted into a class with a high confidence level.

In medical tomography, image reconstruction is generally not unique from a finite number of projections, but the influence of non-uniqueness is avoided in practice where priori knowledge is present that an underlying image is band-limited, and a set of sufficiently many data in reference to the bandwidth can be collected. In the area of compressed sensing, while this technique produces visually pleasing images, tumor-like features may sometimes be hidden or lost. Nevertheless, these features were constructed based on the known imaging geometry and the algorithm, which would not likely be encountered in clinical settings. Most theoretical analyses on compressed sensing methods state the validity of the results with the modifier "with an overwhelming probability". Hence, flaws of deep learning should be very fixable in the same way or insignificant in most cases, because it can be imagined that if the types of training data are sufficiently representative and the structure of a deep network is optimized, prior knowledge (including but not limited to statistical likelihood) can be fully presented for superior image reconstruction.

More aggressively speaking, deep imaging could outperform conventional imaging with statistical, sparsity, and low rank priors, because information processing is nonlinear with a deep network, global through a deeply layered structure, and the best bet with the detailed prior knowledge learned from big data. This is in sharp contrast to many traditional regularizers that are linear, local, or ad hoc. Although the state of the art results obtained with overcomplete wavelet frames or dictionary atoms bear similarities to that with auto-encoders, the wavelet and dictionary based features are both linear and local, and should be theoretically inferior to nonlinear and global representations enabled by a deep network.

Of particular relevance to deep imaging is unsupervised and supervised training of a deep network with big data, or the relationship between big data and deep learning for medical imaging. In the clinical world, there are enormous image volumes but only a limited amount of them were labeled, and patient privacy has been a hurdle for medical imaging research. Nevertheless, the key conditions are becoming ready for big data and deep learning to have an impact on medical imaging research, development, and application. First, big data are gradually accessible to researchers. For example, in the National Lung Screening Trial (NLST) project, over 25,000 patients went through three low-dose CT screenings (T0, T1, and T2) at 1-year intervals, which resulted in more than 75,000 total datasets. Second, deep learning can be implemented via a pre-training step without supervision or a hybrid training process so that intrinsic image features are learned to have favorable initial weights, and then performs backpropagation for fine-tuning. Third, hardware for big data, deep learning, and cloud computing is commercially available and being rapidly improved. Therefore, deep learning can be transferred to medical image reconstruction.

Figure 7:
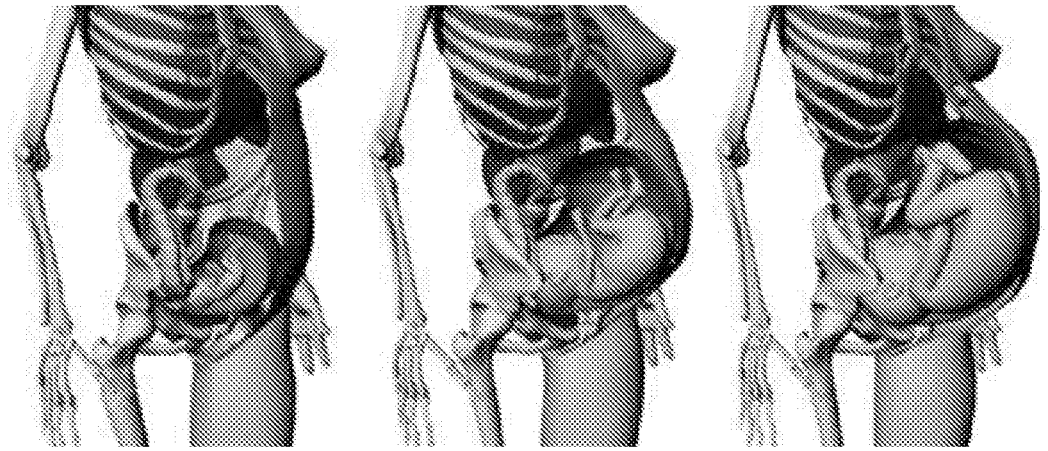
FIG. 7 shows a schematic view of imaging that can be achieved with deep imaging.

Because of the visible human project and other similar efforts, realistic image volumes of the human bodies in different contrasts (e.g., CT and Mill) are readily available. With deformable matching methods, many realistically deformed image volumes can be produced. Also, physiological and pathological features and processes can be numerically added into an image volume or model; see also FIG. 7. Such a synthetic big data could be sufficient for deep imaging.

Supposing that a deep network is well trained, its structure should be stable through re-training with images obtained through locally and finely transformed previously-used images. In other words, moderate perturbation can be an easy mechanism to generate big data. Additionally, this invariance may help characterize the generic architecture of a deep imager.

A deep neural network, and artificial intelligence in general, can be further improved by mimicking neuroplasticity, which is the ability of the brain to grow and reorganize for adaption, learning, and compensation. Currently, the number of layers and the number of neurons per layer in a deep network are obtained using the trial and error approach, and not governed by any theory. In reference to the brain growth and reorganization, the future deep network could work in the same way and become more adaptive and more powerful for medical imaging. As time goes by, it may be possible to design deep networks that are time-varying, reconfigurable, or even have quantum computing behaviors.

Deep learning represents a paradigm shift; from big data with deep learning, unprecedented domain knowledge can be extracted and utilized in an intelligent framework from raw data to final image until clinical intervention. This can be empowered with accurate and robust capabilities to achieve optimal results cost-effectively, even for data that are huge and compromised, as well as for problems that are nonlinear, nonconvex, and overly complicated. It is noted that certain embodiments of the subject invention are related to some aspects of U.S. patent application Ser. No. 15/624,492 (Wang et al., "Methods and Apparatus for X-Genetics"), which is hereby incorporated herein by reference in its entirety.

Figure 6:
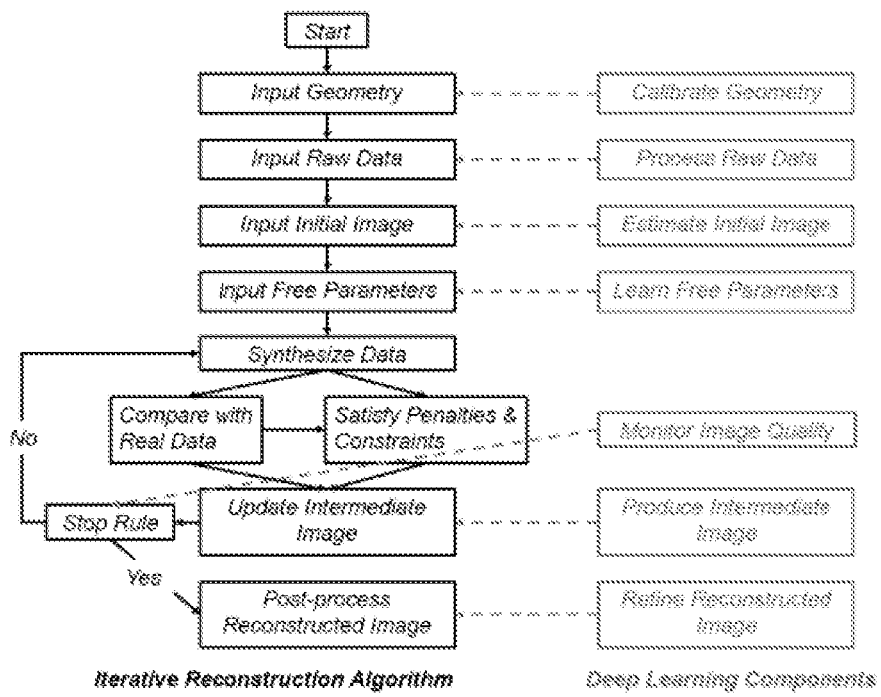
FIG. 6 shows a flowchart for iterative reconstruction, along with multiple machine learning elements that can be brought in at appropriate locations while the corresponding original black box can be knocked out or knocked down.

In an embodiment, one or more machine learning elements of a current image reconstruction scheme can be replaced with deep learning counterparts. To appreciate this replacement strategy, consider genetic engineering techniques. Geneticists use knock-out, knock-down, and knock-in to produce genetically modified models such as genetically modified mice. In a nutshell, knock-out means deletion or mutational inactivation of a target gene; knock-down suppresses the expression of a target gene; and knock-in inserts a gene into a chromosomal locus. Once a target gene is knocked-out, it no longer functions. By identifying the resultant phenotypes, the function of that gene can be inferred. Less brutal than knock-out, knock-down weakens the expression of a gene. On the other hand, knock-in is just the opposite of knock-out. In a similar spirit, each type of reconstruction algorithm can be thought of as an organic flowchart, and some building blocks can be replaced by machine learning counterparts. For example, FIG. 6 shows a generic flowchart for iterative reconstruction, along with multiple machine learning elements that can be knocked-in at appropriate locations while the corresponding original black box can be knocked-out or knocked-down. Thus, a reconstruction algorithm can be used to guide the construction of a corresponding deep network. By the universal approximation theorem, each computational element should have a neural network counterpart. Therefore, a network-oriented equivalent version can be built out of the original algorithm. The real power of the deep learning based reconstruction lies in the data-driven knowledge-enhancing abilities so as to promise a smarter initial guess, more relevant intermediate features, and an optimally regularized final image within an application-specific low-dimensional manifold.

In addition, deep learning based image post-processing can be performed. When a projection dataset is complete, an analytic reconstruction would bring basically full information content from the projection domain to the image space even if data are noisy. If a dataset is truncated, distorted, or otherwise severely compromised (for example, limited angle, few-view, local reconstruction, metal artifact reduction, beam-hardening correction, scatter suppression, and/or motion restoration problems), a suitable iterative algorithm can be used to form an initial image. It is the image domain where the human vision system is good at de-noising, de-streaking, de-blurring, and interpretation. In other words, existing image reconstruction algorithms can be used to generate initial images, and then a deep network can do more intelligent work based on the initial images. This two-stage approach can take advantage of the following: well-established tomographic algorithms can still be utilized; deep networks with images as inputs can be easily adapted; and domain-specific big data can be incorporated as unprecedented prior knowledge. With this approach, the neural network is naturally a nonlinear function because medical image processing and analysis can be effectively performed by a deep network.

Figure 9:
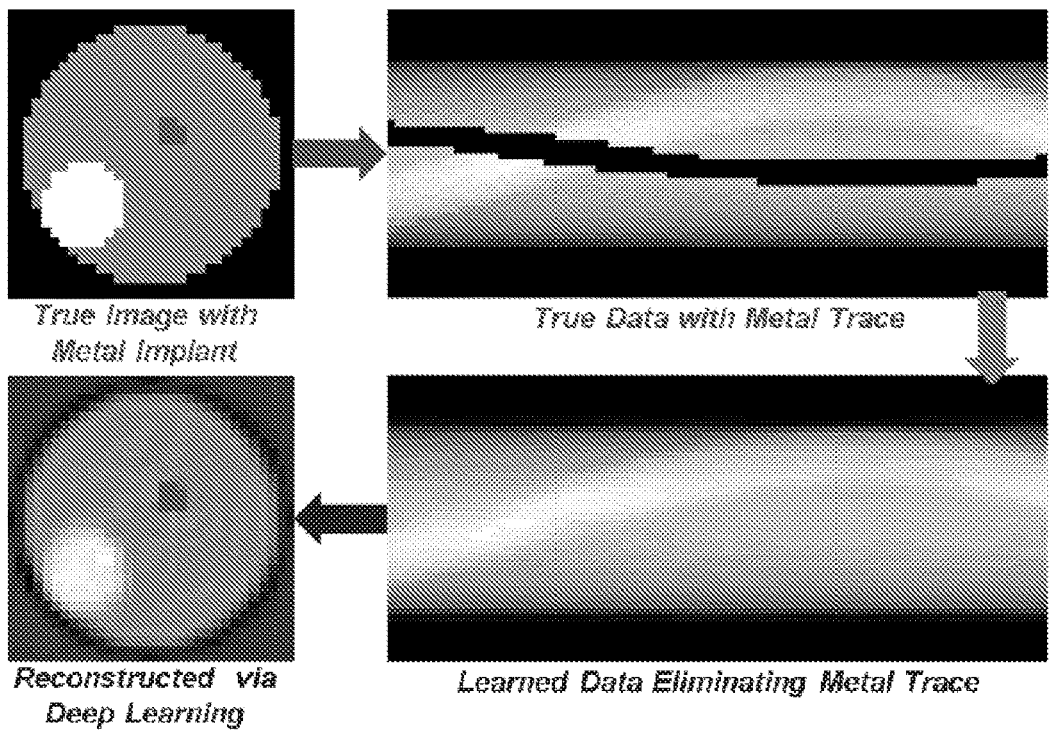
FIG. 9 shows four images demonstrating a deep network capable of sinogram restoration. The top-left image is an original image (metal is the small (purple) dot in the middle), and the top-right image is the associated metal-blocked sinogram for the top-left image. The bottom-right image shows the restored sinogram, and the bottom-left image shows the image that has been reconstructed via deep learning according to an embodiment of the subject invention, demonstrating the potential of deep learning as a smart interpolator over missing data.

Similarly, a sinogram can be viewed as an image, and a deep learning algorithm can be used to improve a low-dose or otherwise compromised sinogram (see, e.g., FIG. 9). The transform from a poor sinogram to an improved one is a type of image processing task, and can be done via deep learning. Then, a better image can be reconstructed from the improved sinogram.

In some embodiments, deep learning can be used without any classic reconstruction algorithm. A broad range of image reconstruction problems can be addressed with imaging performance superior to related art methods.

Deep imaging networks can outperform conventional imaging algorithms because information processing with a deep network is nonlinear in activation functions, global through a deeply layered structure, and a best bet with comprehensive prior knowledge learned from big data. This is in sharp contrast to many traditional regularizers that are linear, local, or ad hoc. Deep neural networks, and artificial intelligence in general, can be further improved by mimicking neuroplasticity, the ability of the brain to grow and reorganize for learning, adaption, and compensation. The number of layers and the number of neurons per layer in a deep network can be obtained using the trial and error approach without the governance of any theory. In reference to the brain growth and reorganization, a deep network could work in the same way and become more adaptive and more suitable for medical imaging. Of particular relevance to deep imaging is how to train a deep network with big data. With unlabeled big data and a smaller or moderate amount of labeled data, deep learning can be implemented via a pre-training step without supervision, a knowledge transfer based initialization, or a hybrid training process, so that intrinsic image features are learned to have favorable initial weights and then fine-tuned. Transfer learning and hybrid training with unlabeled and labeled data could be used. For example, such a training process could be pre-conditioned or guided by an advanced numerical simulator, an observer, and statistical bootstrapping.

With the increasing number of CT scans, the potential radiation risk is a potential concern. Most commercial CT scanners utilize the filtered back projection (FBP) method to analytically reconstruct images, and one of the most used methods to reduce the radiation dose is to lower the operating current of the X-ray tube. However, directly lowering the current significantly degrades the image quality due to the excessive quantum noise caused by an insufficient number of photons in the projection domain. Approaches for improving the quality of low-dose CT images can be categorized as sinogram filtering, iterative reconstruction, or image processing. Sinogram filtering directly smoothens raw data before FBP is applied; and iterative reconstruction solves the problem iteratively, aided by prior information on target images. Types of iterative reconstruction include total variation (TV), nonlocal means (NLM), and dictionary learning. These approaches have difficulty in gaining well-formatted projection data because vendors are not generally open in this aspect, while iterative reconstruction methods often have heavy computational costs. Image processing does not rely on projection data, can be directly applied to low-dose CT images, and can b e easily integrated into the current CT workflow. However, the noise in low-dose CT images does not obey a uniform distribution. As a result, it is not easy to remove image noise and artifacts effectively with traditional image de-noising methods.

Deep learning can efficiently learn high-level features from the pixel level through a hierarchical framework. In an embodiment of the subject invention, a deep convolutional neural network (CNN) can be used to transform low-dose CT images towards corresponding normal-dose CT images. An offline training stage can be used, with a reasonably sized training set. Low-dose CT can be a scan with a dose of, for example, no more than 2.0 millisieverts (mSv), no more than 1.9 mSv, no more than 1.8 mSv, no more than 1.7 mSv, no more than 1.6 mSv, no more than 1.5 mSv, no more than 1.4 mSv, no more than 1.3 mSv, no more than 1.2 mSv, no more than 1.1 mSv, no more than 1.0 mSv, no more than 0.9 mSv, no more than 0.8 mSv, no more than 0.7 mSv, no more than 0.6 mSv, or no more than 0.5 mSv.

Due to the encryption of raw projection data, post-reconstruction restoration is a reasonable alternative for sinogram-based methods. Once the target image is reconstructed from a low-dose scan, the problem becomes image restoration or image de-noising. A difference between low-dose CT image de-noising and natural image restoration is that the statistical property of low-dose CT images cannot be easily determined in the image domain. This can significantly compromise the performance of noise-dependent methods, such as median filtering, Gaussian filtering, and anisotropic diffusion, which were respectively designed for specific noise types. However, learning-based methods are immune to this problem because such methods can be strongly dependent on training samples, instead of noise type (see Examples 3 and 4 for experimental results related to low-dose CT restoration with deep learning).

In an embodiment, deep learning (e.g., a deep neural network) can be used for classification of lung nodules. CT is the imaging modality of choice for evaluation of patients with suspected or known lung cancer, but many lung nodules are benign in etiology. Radiologists rely on several qualitative and quantitative factors to describe pulmonary nodules such as nodule size, shape, margin, attenuation, and location in the lungs. One of the critical nodule characteristics is the classification between malignant and benign nodules, which facilitates nodule staging assessment and consequent therapeutic planning. Related art nodule analysis, mostly based on handcrafted texture feature extractors, suffers from the need of specialized knowledge in selecting parameters and robustness to different datasets. However, the deep features extracted from deep neural networks are more general and high-level compared with handcrafted ones. Training a deep neural network, though, can in some cases require massive data for avoiding overfitting, which may be infeasible for a small dataset such as the lung image database consortium (LIDC) and image database resource initiative (IDRI) (LIDC-IDRI). In some embodiments, transfer learning can be used to apply a deep neural network to a small dataset by taking a pre-trained deep neural network on a large-scale dataset as a feature extractor for a task of interest. Knowledge can be transferred from general object recognition tasks to classification tasks in a similar category.

Transfer learning from pre-trained deep neural networks can be applied on a large-scale image classification dataset, such as ImageNet (see Reference [121], which is incorporated by reference herein in its entirety), for lung nodule classification. To improve transferability, fine-tuning and feature selection techniques can be employed to make deep features more suitable for lung nodule classification. More specifically, the fine-tuning technique can retrain a deep neural network using lung nodule data, and feature selection can capture a useful subset of features for lung nodule classification. Experimental results confirm that the classification performance can be improved through fine-tuning and feature selection techniques and that the results outperform handcrafted texture descriptors (see Example 5).

In an embodiment, deep learning (e.g., a deep neural network) can be used to reduce artifacts (e.g., metal streak artifacts) in CT images. Metal artifacts are a long-standing problem in CT that severely degrade image quality. Existing metal artifact reduction (MAR) techniques cannot be translated to clinical settings. For those algorithms that have been adopted clinically, there remain important applications in which a sufficient image quality cannot be achieved, such as for proton therapy planning. Tumor volume estimation is very sensitive to image reconstruction errors, and miscalculation due to metal artifacts may result in either tumor recurrence or radiation toxicity. Normalization-based MAR (NMAR) is considered a state-of-the-art method that employs interpolation and normalization to correct data in the metal trace (see Reference [79], which is incorporated by reference herein in its entirety).

Deep networks, such as a CNN, are powerful in their ability to extract detailed features from large datasets, enabling great successes in image processing and analysis. In a supervised learning process, the network can be trained with labeled data/images to learn how to map features between the input and the label. Once trained, the network can use forward prediction to estimate an output given an unlabeled input. Embodiments can reduce streak artifacts in critical image regions outside the metal object by combining a CNN with a state-of-the-art NMAR method. The network can be trained to create an end-to-end mapping of patches from metal-corrupted CT images to their corresponding artifact-free ground truth. Because raw projection data is not always accessible in commercial scanners, experiments have been performed via numerical simulation to demonstrate the feasibility and merits of deep learning for MAR (see Example 6).

In an embodiment, sinograms based on deep learning (e.g., a deep neural network) can be used to reduce artifacts (e.g., metal streak artifacts) in CT images. Deep learning can be used for the purpose of sinogram completion in CT, which has particular application in the field of MAR, but may also be used to address the effects of projection data truncation and other issues in medical imaging.

Sinogram completion based methods is a main category of MAR approaches, with iterative methods representing the second main group. Sinogram completion (also referred to as sinogram-interpolation, or in-painting) methods generally discard the projection data that corresponds to rays within the metal trace, and replace this "missing data" with an estimate. In an ideal case the estimated data represents a good approximation of projection data that reflects the entire shape and internal structure of the imaged object, with the exception only of the metal implant (or other metal object) itself. Specifically, structures within the object are typically represented (depending on the specific shape of the structure) by generally sinusoidal traces in the sinogram. The estimated data in the missing data region should appropriately reflect this characteristic behavior, otherwise the reconstructed image will be impacted by associated streaks or banding artifacts. In some instances, additional artifacts can be created, through the MAR processing, that were not present in the image before correction.

In pure projection-based interpolation approaches the missing data is estimated based on interpolation within the sinogram domain, while some other sinogram completion approaches utilize an initial reconstruction (e.g., using a few iterations) to produce a first estimate of the structure of the imaged object, which (after re-projection) helps in obtaining an improved sinogram interpolation.

In embodiments of the subject invention, missing data in the sinogram itself can be estimated without employing an initial reconstruction step. Similar to the approach taken in other pure sinogram-based interpolation schemes, the missing data is estimated for a single view (or a small set of adjacent views) from a detector region that is adjacent to the missing data region (i.e., from data corresponding to detector channels that are adjacent to the missing data region on both sides), and from views corresponding to an angular interval around the current view angle. This estimation process can be implemented in a straightforward way as a simple fully connected neural network. A simple CNN can be used, such as one comprising a set of analysis filters (as the first layer), followed by a mapping of the resulting feature maps into a mapped feature space (as a second layer), which is then followed by a second convolution with appropriate "synthesis filters" and summation of the resultant images (as a third and final layer). The first layer can be interpreted as an extraction of image features (e.g., extracted from regions of the sinogram that are located adjacent to the missing-data region to be estimated), followed by a mapping of features and a "synthesis" of the missing data from the mapped features as the last layer.

In embodiments of the subject invention, a deep learning technique can be applied to produce mono-energetic sinograms of any energy from dual-energy sinogram measurements. A convolutional neural network (CNN) can be developed to link a dual-energy CT sinograms to a mono-energetic sinogram. By training a CNN network using a large number of image patches, the CNN can find an intrinsic connection between the input dual-energy images and the corresponding mono-energetic sinogram.

In many embodiments, a deep learning algorithm used for image reconstruction can have more than three layers and/or can comprise two or more sub-networks.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A method of reconstructing an image from tomographic data (e.g., obtained by a biomedical imaging process, non-destructive evaluation, or security screening), the method comprising:
performing at least one algorithm on a raw data set of the tomographic data to obtain a reconstructed image, the at least one algorithm comprising a deep learning algorithm.

Embodiment 2

The method according to embodiment 1, wherein performing at least one algorithm on the raw data to obtain a reconstructed image comprises:
performing at least one conventional, non-deep-learning algorithm on the raw data to obtain an initial image; and
performing a deep learning algorithm on the initial image to obtain the reconstructed image.

Embodiment 3

The method according to embodiment 1, wherein performing at least one algorithm on the raw data to obtain a reconstructed image comprises performing a deep learning algorithm directly on the raw data to obtain the reconstructed image.

Embodiment 4

The method according to any of embodiments 1-3, wherein the deep learning algorithm is performed by a deep network.

Embodiment 5

The method according to embodiment 4, wherein the deep network is a deep neural network.

Embodiment 6

The method according to any of embodiments 1-5, wherein the deep learning algorithm is performed by a convolutional neural network (CNN).

Embodiment 7

The method according to any of embodiments 4-6, further comprising training the deep network with a training set of final images, prior to performing the deep learning algorithm.

Embodiment 8

The method according to any of embodiments 1-7, wherein raw data is obtained by computed tomography (CT), magnetic resonance imaging (MM), single-photon emission computed tomography (SPECT), or positron emission tomography (PET).

Embodiment 9

The method according to any of embodiments 1-8, wherein performing at least one algorithm on the raw data to obtain a reconstructed image comprises performing a deep learning algorithm to complete a sinogram based on the raw data.

Embodiment 10

The method according to any of embodiments 2 and 4-9, wherein the at least one conventional, non-deep-learning algorithm comprises a normalization-based metal artifact reduction (NMAR) algorithm.

Embodiment 11

The method according to any of embodiments 1-10, wherein the raw data includes at least one metal artifact and the reconstructed image includes metal artifact reduction (MAR) compared to the raw data.

Embodiment 12

The method according to any of embodiments 1-11, wherein the deep learning algorithm is performed by a deep neural network, the deep neural network being AlexNet.

Embodiment 13

The method according to any of embodiments 1-11, wherein the deep learning algorithm is performed by a deep neural network, the deep neural network being ResNet.

Embodiment 14

The method according to any of embodiments 1-11, wherein the deep learning algorithm is performed by a deep neural network, the deep neural network being GoogleNet.

Embodiment 15

The method according to any of embodiments 1-11, wherein the deep learning algorithm is performed by a deep neural network, the deep neural network being AlexNet, ResNet, or GoogleNet.

Embodiment 16

The method according to any of embodiments 1-7 and 9-15, wherein the raw data comprises a CT image of one or more lung nodules.

Embodiment 17

The method according to any of embodiments 1-7 and 9-16, wherein the raw data comprises a low-dose CT image (a CT image obtained by a low-dose CT scan; the term "low-dose" can mean, e.g., no more than 2.0 millisieverts (mSv), no more than 1.9 mSv, no more than 1.8 mSv, no more than 1.7 mSv, no more than 1.6 mSv, no more than 1.5 mSv, no more than 1.4 mSv, no more than 1.3 mSv, no more than 1.2 mSv, no more than 1.1 mSv, no more than 1.0 mSv, no more than 0.9 mSv, no more than 0.8 mSv, no more than 0.7 mSv, no more than 0.6 mSv, or no more than 0.5 mSv).

Embodiment 18

The method according to any of embodiments 1-17, wherein the deep learning algorithm reduces noise of the raw data such that the reconstructed image has less noise than does the raw data.

Embodiment 19

The method according to any of embodiments 2 and 4-18, wherein the at least one conventional, non-deep-learning algorithm comprises a filtered back projection (FBP) algorithm.

Embodiment 20

The method according to any of embodiments 2 and 4-19, wherein the at least one conventional, non-deep-learning algorithm comprises a model-based image reconstruction (MBIR) algorithm.

Embodiment 21

The method according to any of embodiments 1-20, wherein the deep learning algorithm comprises more than three layers.

Embodiment 22

The method according to any of embodiments 1-21, wherein the deep learning algorithm comprises two or more sub-networks.

Embodiment 23

A method for reconstructing an image from tomographic data obtained in an imaging process for any purpose (e.g., as biomedical imaging, non-destructive evaluation, and security screening), the method comprising:
performing at least one algorithmic step on a raw data-set or intermediate data-set (e.g., a processed sinogram or k-space data-set or an intermediate image) to obtain a final reconstructed image, the algorithmic step being from a machine learning algorithm (e.g., a deep learning algorithm that has more than three layers and/or comprises two or more sub-networks).

Embodiment 24

A system for reconstructing an image from raw data obtained by a medical imaging process, the system comprising:
a subsystem for obtaining medical imaging raw data;
at least one processor; and
a (non-transitory) machine-readable medium (e.g., a (non-transitory) computer-readable medium), in operable communication with the subsystem for obtaining medical imaging raw data and the at least one processor, having machine-executable instructions (e.g., computer-executable instruction) stored thereon that, when executed by the at least one processor, perform the method according to any of embodiments 1-23.

Embodiment 25

The system according to embodiment 24, wherein the subsystem for obtaining medical imaging raw data comprises a CT scanner.

Embodiment 26

The system according to any of embodiments 24-25, wherein the subsystem for obtaining medical imaging raw data comprises a PET scanner.

Embodiment 27

The system according to any of embodiments 24-26, wherein the subsystem for obtaining medical imaging raw data comprises an MII machine.

Embodiment 28

The system according to any of embodiments 24-27, wherein the subsystem for obtaining medical imaging raw data comprises an SPECT machine.

Embodiment 29

The method according to any of embodiments 1-23 or the system according to any of embodiments 24-28, wherein the raw data comprises features.

Embodiment 30

The method according to any of embodiments 7-23 or the system according to any of embodiments 24-29, wherein training the deep network comprises performing at least one fine-tuning technique and/or at least one feature selection technique on the deep network.

A greater understanding of the embodiments of the present invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

Figure 8:
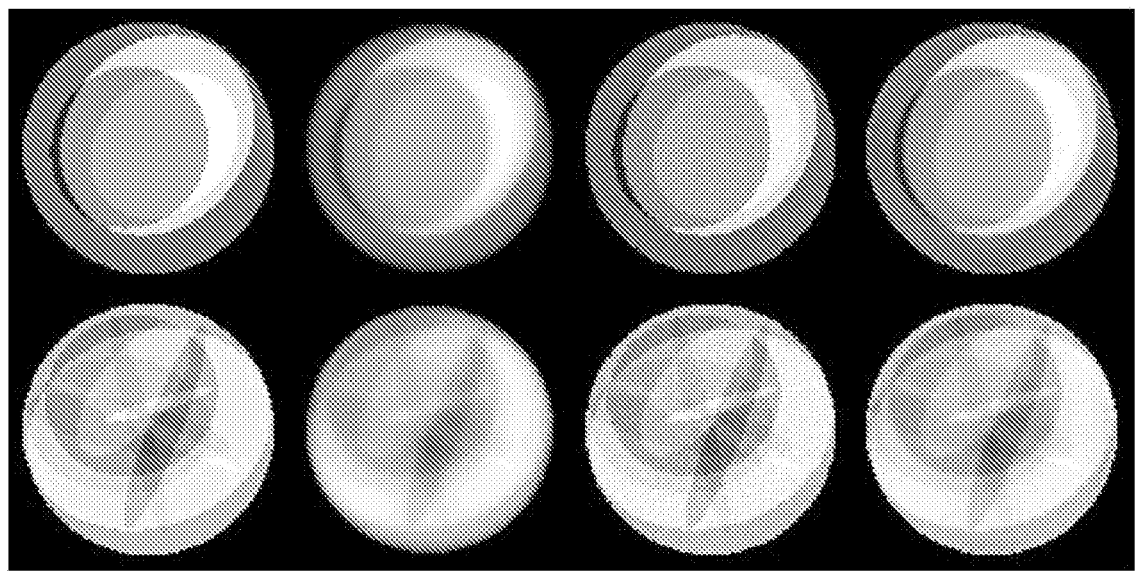
FIG. 8 shows eight images demonstrating a deep network capable of iterative reconstruction. The image pair in the left-most column are two original phantoms; the image pair in the second-from-the-left column are the simultaneous algebraic reconstruction technique (SART) reconstruction after 20 iterations; the image pair in the second-from-the-right column are the SART reconstruction after 500 iterations; and the image pair in the right-most column are the deep imaging results after starting with the corresponding 20-iteration image (from the second-from-the-left column) as the inputs, which are very close to the 500-iteration images, respectively.

An image reconstruction demonstration with deep learning was performed. A poor-quality initial image was reconstructed to a good-quality image. A 2D world of Shepp-Logan phantoms was defined. A field of view was a unit disk covered by a 128*128 image, 8 bits per pixel. Each member image was one background disk of radius 1 and intensity 100 as well as up to 9 ellipses completely inside the background disk. Each ellipse was specified by the following random parameters: center at (x, y), axes (a, b), rotation angle q, and intensity selected from [−10, 10]. A pixel in the image could be covered by multiple ellipses including the background disk. The pixel value is the sum of all the involved intensity values. From each image generated, 256 parallel-beam projections were synthesized, 180 rays per projection. From each dataset of projections, a simultaneous algebraic reconstruction technique (SART) reconstruction was performed for a small number of iterations. This provided blurry intermediate images. Then, a deep network was trained using the known original phantoms to predict a much-improved image from a low-quality image. FIG. 8 shows the results of this demonstration. The image pair in the left-most column are two original phantoms; the image pair in the second-from-the-left column are the SART reconstruction after 20 iterations; the image pair in the second-from-the-right column are the SART reconstruction after 500 iterations; and the image pair in the right-most column are the deep imaging results after starting with the corresponding 20-iteration image (from the second-from-the-left column) as the inputs, which are very close to the 500-iteration images, respectively. In fact, the deep imaging results could be considered better than the 500-iteration images.

Example 2

Another image reconstruction demonstration with deep learning was performed. A poor-quality sinogram was reconstructed to a good-quality sinogram, which was prepared in a way similar to that for Example 1. Each phantom contained a fixed background disk and two random disks inside the circular background; one disk represents an X-ray attenuating feature, and the other an X-ray opaque metal part. The image size was made 32×32 for quick results. After a phantom image was created, the sinogram was generated from 90 angles. Every metal-blocked sinogram was linked to a complete sinogram formed after the metal was replaced with an X-ray transparent counterpart. Then, a deep network was trained with respect to the complete sinograms to restore missing data. FIG. 9 shows the results of this demonstration. Referring to FIG. 9, the top-left image is an original image (metal is the small (purple) dot in the middle), and the top-right image is the associated metal-blocked sinogram for the top-left image. The bottom-right image shows the restored sinogram, and the bottom-left image shows the image that has been reconstructed via deep learning according to an embodiment of the subject invention, demonstrating the potential of deep learning as a smart interpolator over missing data.

Example 3

Figure 10:
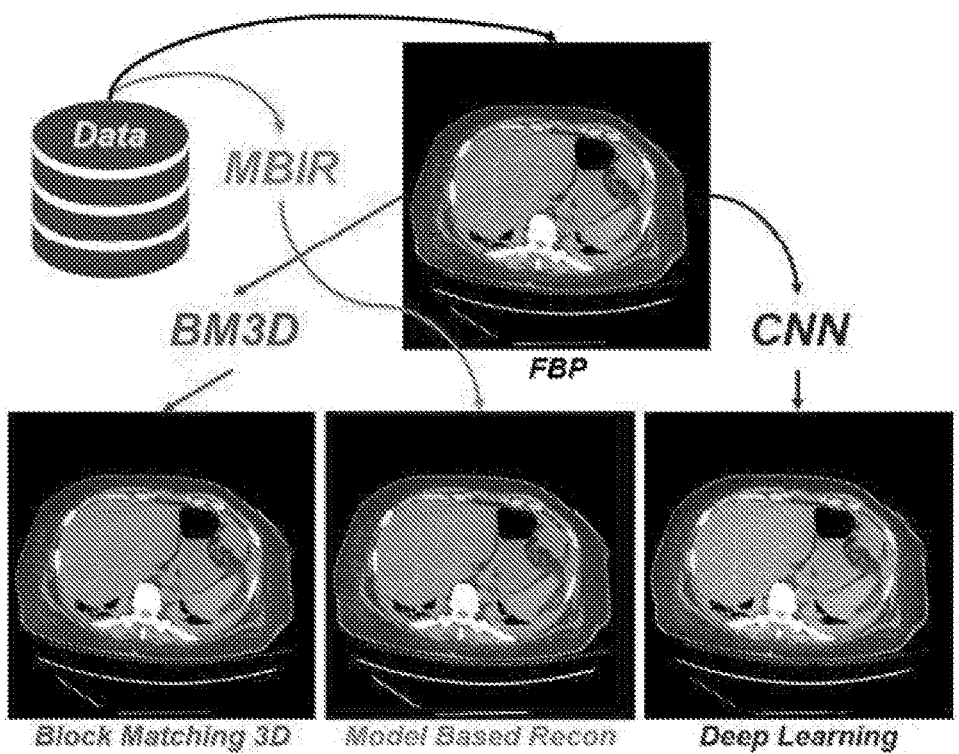
FIG. 10 shows a representation of a data block and also four images, demonstrating deep-learning-based image de-noising. The top-left portion is the representation of the data block, and the top-right image shows a filter back projection (FBP) image. The bottom-left image shows a reconstructed image using block matching 3D, the bottom-middle image shows a reconstructed image using model-based image reconstruction (MBIR), and the bottom-right image shows a reconstructed image using deep learning (e.g., via a convolutional neural network (CNN)) according to an embodiment of the subject invention. This demonstrates that the deep learning reconstruction is an efficient alternative to state of the art iterative reconstructive strategies.
Figure 11:
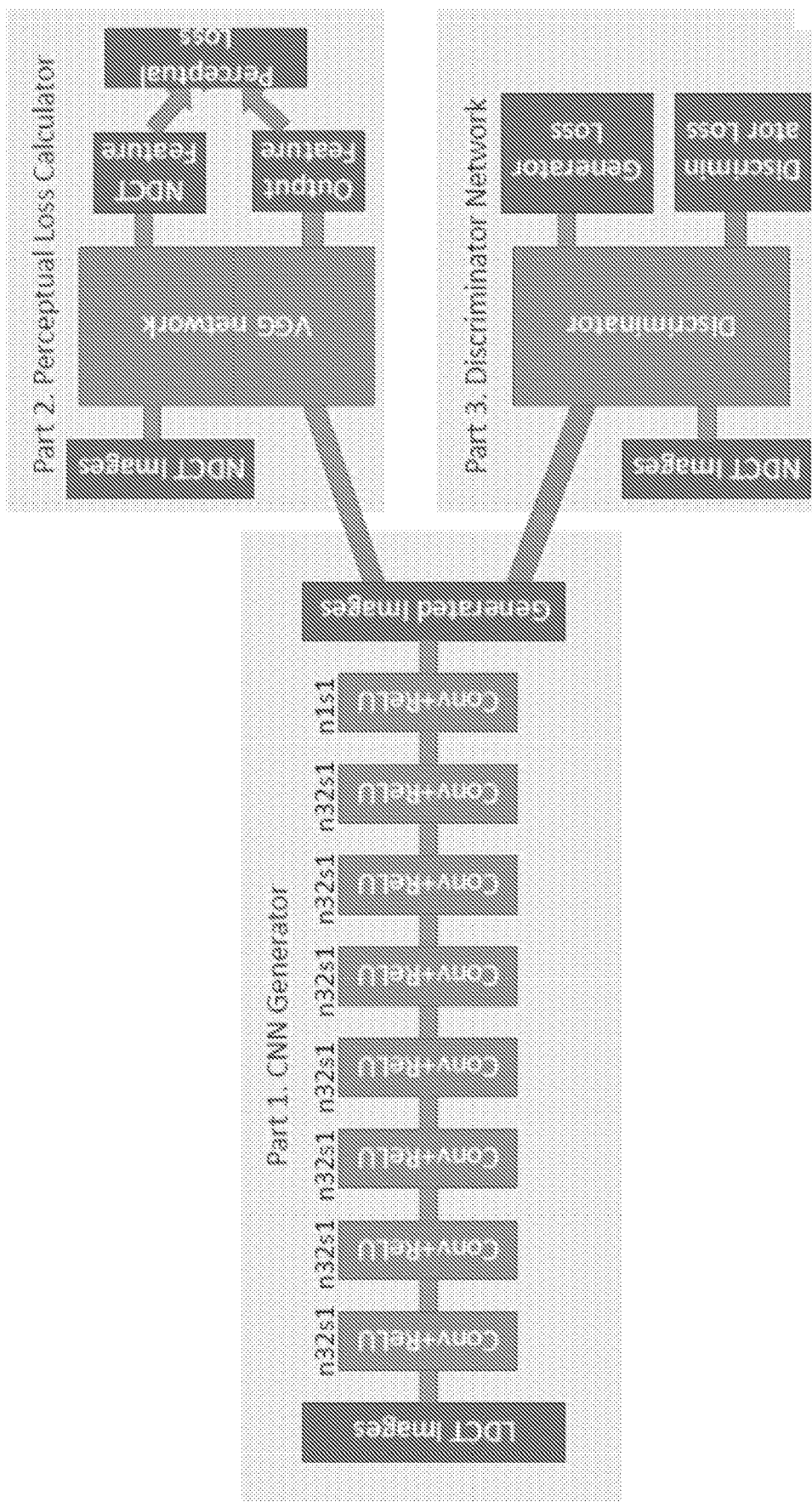
FIG. 11 shows a schematic view of the architecture of a generative adversarial network (GAN) network that can be used for CT image reconstruction according to an embodiment of the subject invention. The GAN of FIG. 11 includes three parts. The first part is the generator, which can be a plain convolutional neural network (CNN). The second part of the network is the perceptual loss calculator, which can be realized by using the pre-trained VGG network. A denoised output image from the generator and the ground truth image are fed into the pre-trained VGG network for feature extraction. Then, the objective loss can be computed using the extracted features from a specified layer. The reconstruction error can then be back-propagated to update the weights of the generator only, while keeping the VGG parameters intact. The third part of the network is the discriminator. It can be trained to correctly discriminate between the real and generated images. During the training, the generator and the discriminator can be trained in an alternating fashion.

Another image reconstruction demonstration with deep learning was performed to demonstrate the potential of deep learning with MGH Radiology chest CT datasets. These datasets were acquired in low dose levels. They were reconstructed using three reconstruction techniques: filtered back-projection (FBP), adaptive statistical iterative reconstruction (ASIR), and model-based iterative reconstruction (MBIR). These were all implemented on commercial CT scanners. The same deep learning procedure was followed as in Examples 1 and 2, and the FBP image was used as input. The MBIR image was taken as the gold standard for neural network training. For comparison, image de-noising was performed on the FBP image using the block matching and 3D filtering (BM3D) method and the deep neural network method according to an embodiment of the subject invention. FIG. 10 shows the image de-noising effect of deep learning, as compared to the MBIR counterpart. In FIG. 10, the top-left portion is the representation of the data block, and the top-right image shows the FBP image. The bottom-left image shows the reconstructed image using BM3D, the bottom-middle image shows the reconstructed image using MBIR, and the bottom-right image shows the reconstructed image using deep learning (e.g., via a convolutional neural network (CNN)).

FIG. 10 demonstrates that the deep learning reconstruction is an efficient alternative to MBIR, but deep learning is much faster than the state of the art iterative reconstruction. A computationally efficient post-processing neural network after the standard "cheap" FBP achieves a very similar outcome as the much more elaborative iterative scheme, and yet the neural network solution does not need any explicit physical knowledge such as the X-ray imaging model.

Example 4

Figure 12:
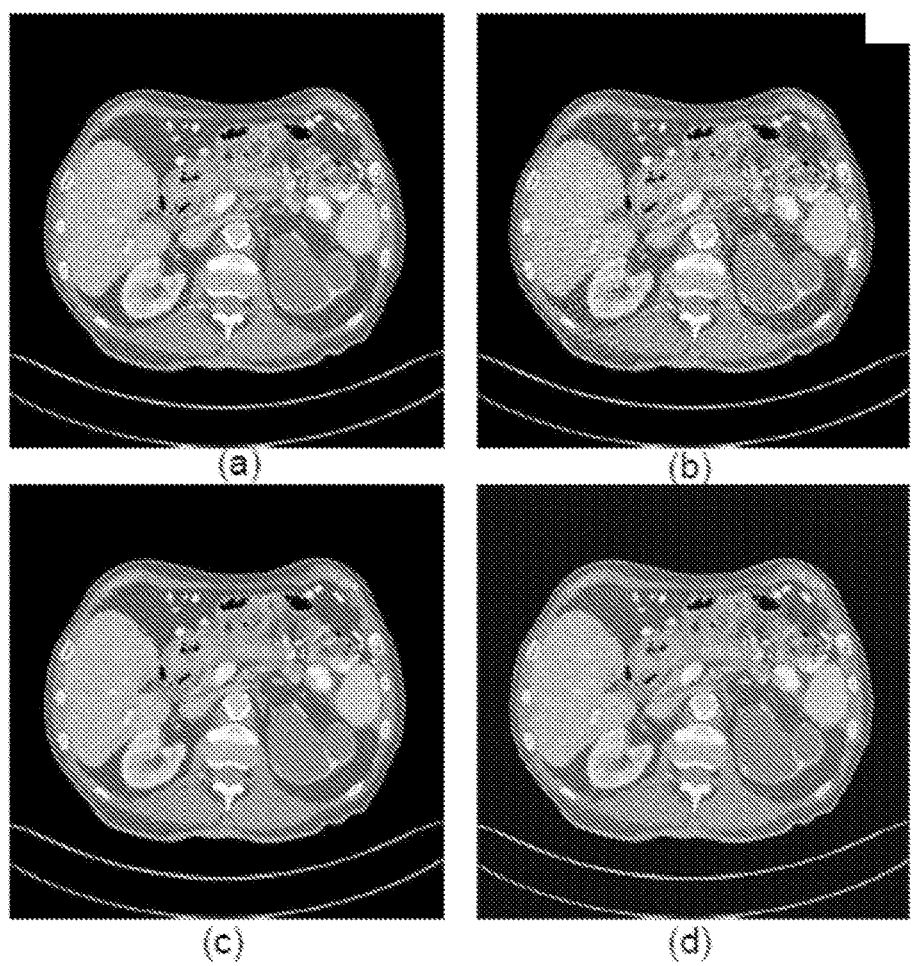
FIGS. 12A-12D show results of image reconstruction of abdomen images.

Another image reconstruction demonstration with deep learning was performed to demonstrate the potential of deep learning with the datasets for "The 2016 NIH AAPM Mayo Clinic Low Dose CT Grand Challenge". An improved network structure under generative adversarial network (GAN) with perceptual loss was evaluated in this example. The dataset contained abdominal CT images of normal dose from 10 anonymous patients and simulated quarter-dose CT images. In the experiment, 100,096 pairs of image patches were randomly extracted from 4,000 CT images as the training inputs and labels. The patch size was 64×64. FIGS. 12A-12D show the image de-noising effect of GAN, as compared to a plain CNN network. FIG. 12A shows a normal dose CT image; FIG. 12B shows a quarter dose image of the same abdomen; FIG. 12C shows the result of image reconstruction using a CNN network with MSE loss; and FIG. 12D shows the result of image reconstruction result using the WGAN framework with perceptual loss.

Example 5

Experiments were run to test the performance of a deep neural network on classification of lung nodules according to an embodiment of the subject invention. The LIDC-IDRI dataset (see Reference [119], which is incorporated by reference herein in its entirety) consists of diagnostic and lung cancer screening thoracic CT scans with annotated lung nodules from a total number of 1,010 patients. Each nodule was rated from 1 to 5 by four experienced thoracic radiologists, indicating an increasing probability of malignancy. In the experiments, the ROI of each nodule was obtained along with its annotated center in accordance with the nodule report, with a square shape of a doubled equivalent diameter. An average score of a nodule was used for assigning probability of malignant etiology. Nodules with an average score higher than 3 were labeled as malignant, and nodules with an average score lower than 3 were labeled as benign. Some nodules were removed from the experiments in the case of the averaged malignancy score being rated by only one radiologist. To sum up, there were 959 benign nodules and 575 malignant nodules. The size of benign ROIs ranged from 8 to 92 pixels, with a mean size of 17.3 and a standard deviation of 7.0 pixels. The size of malignant ROIs ranged from 12 to 95 pixels, with a mean size of 35.4 and a standard deviation of 15.8 pixels.

AlexNet is a convolutional neural network (CNN) model (see Reference [87], which is incorporated by reference herein in its entirety) including five convolutional layers, three pooling layers, two local response normalization (LRN) layers, and three fully connected layers. A publicly available version of AlexNet was pre-trained on the large-scale. The ImageNet dataset ([121]), which contains one million images and one thousand classes, was used. The weights of pre-trained AlexNet were pre-trained and used in the experiments.

Figure 14:
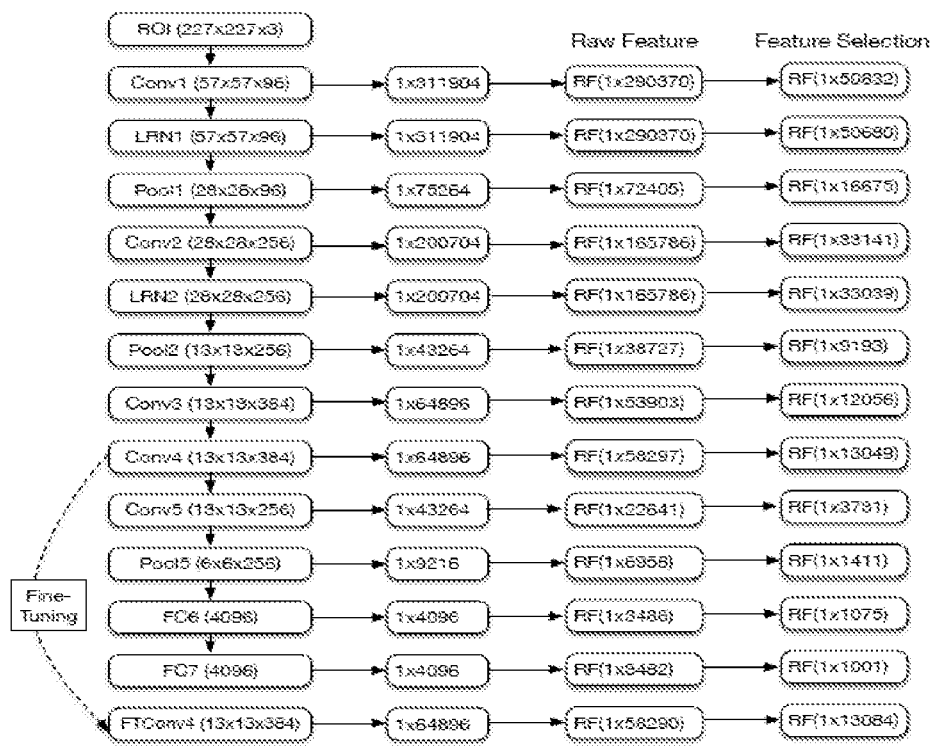
FIG. 14 shows a schematic view of extracting deep features through fine-tuning and feature selection.
Figure 15:
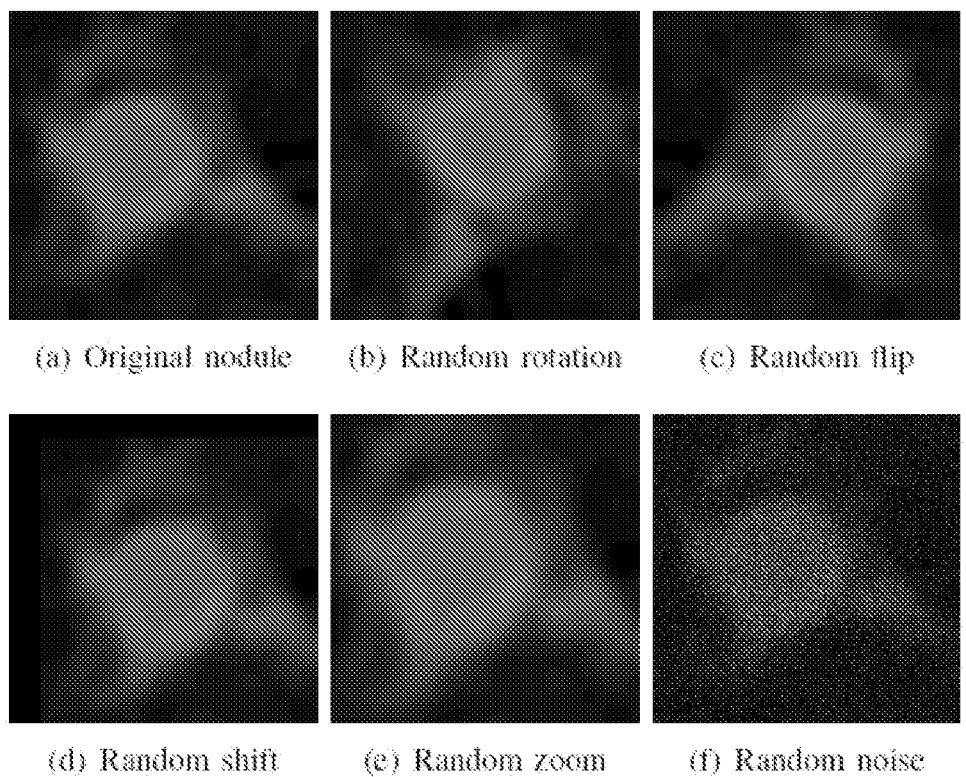
FIGS. 15A-15F show data augmentation of a lung nodule.

The pre-trained AlexNet was used to extract deep features from ROIs of the lung nodules. After removing the last fully connected layer for classification into 1,000 classes, each layer of the AlexNet would be a feature extractor. This is to say that 12 different deep features can be extracted from one ROI. The process of extracting features is depicted in FIG. 14. The first column indicates the architecture of AlexNet, and the numbers in the second column denote the dimensions of flatten features extracted from all the layers of AlexNet. Those flatten features after eliminating all zero-variance columns were used to train Random Forest (RF) classifiers (see Reference [122], which is incorporated by reference herein in its entirety), which were in the third column and called raw features. In FIG. 14, from left to right, the columns indicate the architecture of the pre-trained AlexNet, the flattened deep features, deep features with eliminating all zero-variance columns (raw feature), and deep features after feature selection. The last row is the fine-tuned Conv4. The deep feature at the lower right corner was obtained by 1) fine-tuning Conv4, 2) eliminating zero-variance columns, and 3) extracting a subset through feature selection.

Deep features extracted from earlier layers of deep neural networks can be more generalizable (e.g., edge detectors or color blob detectors), and that should be useful for many tasks. Those features extracted from later layers, however, become progressively more specific to the details of the classes contained in the original dataset. In the case of ImageNet, which includes many dog breeds, a significant portion of the representative power of AlexNet may be devoted to features that are specific to differentiating between dog breeds. Due to the difference between the lung nodule dataset and ImageNet, it was not clear which layer would be more suitable for lung nodule classification. Therefore, features from all the layers were evaluated.

It should be noted that a pre-trained neural network does not necessarily contain any specific information about a lung nodule. To enhance the transferability from the pre-trained CNN (e.g., AlexNet), the CNN can be fine-tuned and feature selection can be applied to adapt the CNN for a specific purpose (e.g., lung nodule classification). Fine-tuning can be applied not only to replace and retrain the classifier on the top of the CNN (e.g., AlexNet) using the lung nodule dataset but also to fine-tune the weights of the pre-trained CNN (e.g., AlexNet) through the backpropagation.

In view of the classification accuracy reported below, features obtained from Conv4 were more suitable for lung nodule classification than those of other layers. The layers after Conv4 were replaced with a fully connected layer as the binary classifier. Due to the concern of overfitting, only Conv4 was tuned, and the lung nodule data was enlarged for retraining. Methods for enlarging lung nodule data included random rotation, random flip, random shift, random zoom, and random noise. FIGS. 15A-15F shows the data augmentation results for a lung nodule in the experiments. The fine-tuned Conv4, called FTConv4, is shown in the last row of FIG. 14.

Figure 16:
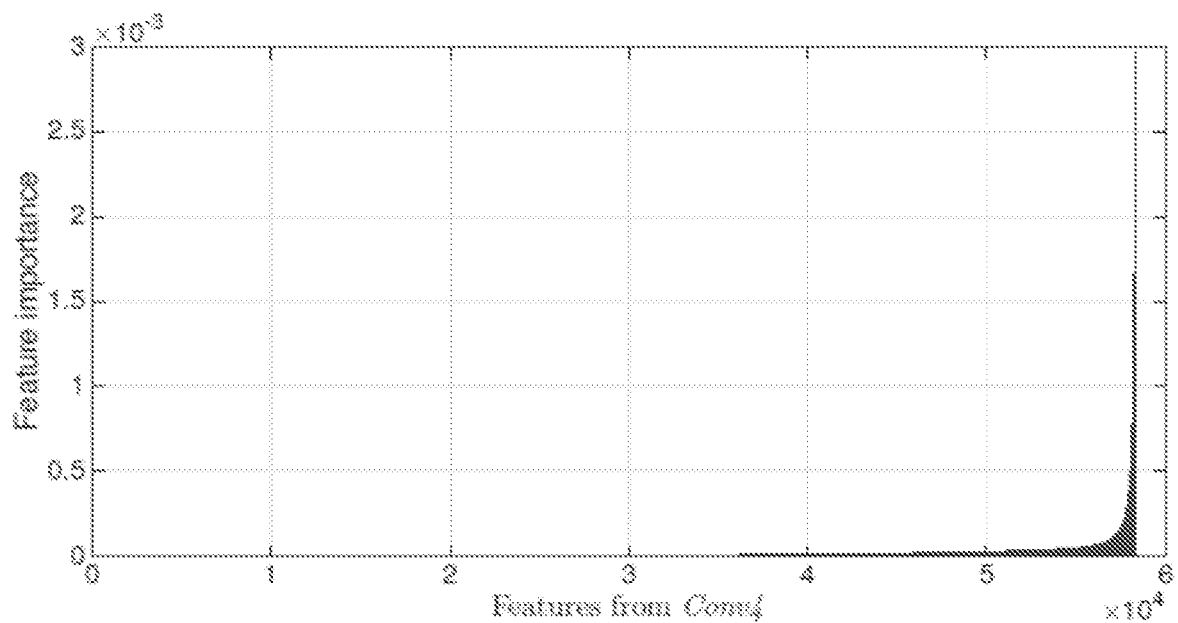
FIG. 16 shows a plot of feature importance versus number of deep features extracted by Conv4.

Deep features extracted from AlexNet suffer from the curse of the dimensionality and are redundant to lung nodule classification, even after Conv4 was fine-tuned with the lung nodule dataset. As an example using Conv4, after removing the zero-variance columns, one ROI was represented by a 58,297-dimensional vector. Using the feature importance measurement provided by RF classifier, there were 26,842 columns with feature importance of zero to lung nodule classification as shown in FIG. 16. That is, almost half of the features extracted from Conv4 were irrelevant to the classification of lung nodules. The feature importance was computed with the random forest classifier, which in turn was used to discard irrelevant features. Those columns with importance scores higher than the averaged importance score were kept as the relevant features for lung nodule classification, as shown in the last column in FIG. 14.

Each ROI was up-sampled into 227×227×3 and then fed into AlexNet. It should be noted that each ROI had three channels despite being grayscale to fit the AlexNet which was originally designed for color images. For evaluating the performance of extracted features, ROIs were randomly divided into a training set with 60% of the lung nodules and a testing set with the remaining lung nodules. The random forest classifier was trained on the training set, the classification accuracy was calculated for the test. The reported results were averaged on 50 repetitions. The RF classifier was taken from the scikit-learn package ([123]).

Figure 17:
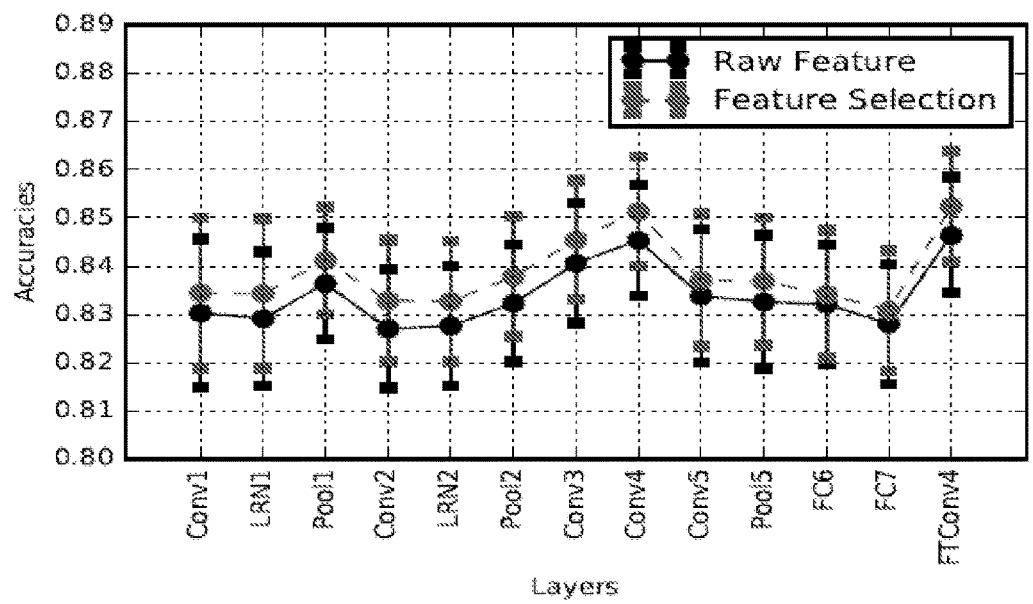
FIG. 17 shows a plot of classification accuracy with deep features extracted from each layer. For each vertical line, starting from the bottom and moving upwards, the raw feature is indicated by the first dash, the first dot, and the third dash, while the feature selection is indicated by the second dash, the second dot, and the fourth dash. That is, the feature selection in each case is more accurate than the raw feature.

FIG. 17 presents the classification accuracies with raw features extracted from each layer of the pre-trained AlexNet and fine-tuned Conv4 on the lung nodule dataset as well as the deep features after feature selection. For each vertical line in FIG. 17, starting from the bottom and moving upwards, the raw feature is indicated by the first dash, the first dot, and the third dash, while the feature selection is indicated by the second dash, the second dot, and the fourth dash. That is, the feature selection in each case is more accurate than the raw feature. Referring to FIG. 17, the features extracted from Conv4 outperform those from the other layers. Features from layers earlier than Conv4 were insufficient to characterize the lung nodules, and features from layers later than Conv4 were more specific to their original dataset, leading to slight performance decrease.

To enhance the transferability of the pre-trained AlexNet, FIG. 17 also presents the classification accuracies using fine-tuning and feature selection techniques. The results from fine-tuned Conv4, FTConv4, are shown at the far-right of FIG. 17. After fine-tuning AlexNet on the lung nodule data, the classification accuracy was slightly improved compared to Conv4. However, feature selection can significantly improve the classification accuracy. Compared with the parameters of Conv4, the lung nodule dataset was still too small to fine-tune AlexNet, and most of the features extracted from Conv4 were irrelevant to lung nodule classification, which increased the difficulty in retraining AlexNet. Also, feature selection can remove those irrelevant features and extract a useful subset of features for classification. The best classification accuracy was achieved with the deep features from FTConv4 after feature selection.

The results were compared with two handcrafted texture descriptors including the local binary pattern (LBP) ([113]) and the histogram of gradient (HOG) ([114]). LBP and HOG were sensitive to window size and number of neighborhood points, respectively. 3-fold cross-validation was used to tune these two parameters. The averaged results are shown in Table I. LBP and HOG were copied from the scikit-image package ([124]). The feature extracted from Conv4 with fine-tuning and feature selection plainly outperformed the handcrafted texture descriptors. Although deep neural networks such as GoogleNet and ResNet (from References [116] and [117], respectively, both of which are incorporated by reference herein in their entireties) can perform better than AlexNet for ImageNet classification, AlexNet was used in the experiments due to its simplicity and rich literature.

TABLE I

COMPARISON WITH BASELINE ALGORITHMS

| Method | LBP | HOG | FTConv4 |
|---|---|---|---|
| Accuracy | 0.799 ± 0.013 | 0.838 ± 0.012 | 0.852 ± 0.011 |

Example 6

Numerical simulations were performed to demonstrate the feasibility and merits of deep learning for MAR according to an embodiment of the subject invention. All training and test data for the CNN were generated using industrial CT simulation software, CatSim (General Electric Global Research Center, Niskayuna, N.Y.) ([89]). Simple hip phantoms were defined with elliptical areas of water and bone in random aspect ratios. A metal ellipse of either titanium or stainless steel was set near each bone region to represent the hip implants. Two scans were simulated for each phantom based on a GE LightSpeed VCT system architecture. The first scan followed a standard clinical protocol, with key parameters including a tube voltage of 120 kVp, a tube current of 300 mA, 108 photons, 300 detectors, and 360 views at uniform projection angles between 0-360 degrees. The 512×512 reconstructed image contained severe artifacts. For the initial correction, the image was reconstructed using the NMAR algorithm. This NMAR result served as the input to the CNN. A second scan on each phantom was simulated with the same parameters, except that a sufficiently higher number of photons were assigned a single energy of 70 keV to generate a mono-energetic image without artifacts. This served as the ground truth and target of the CNN. A total of 5,000 phantoms containing titanium or stainless steel implants were scanned.

Figure 18:
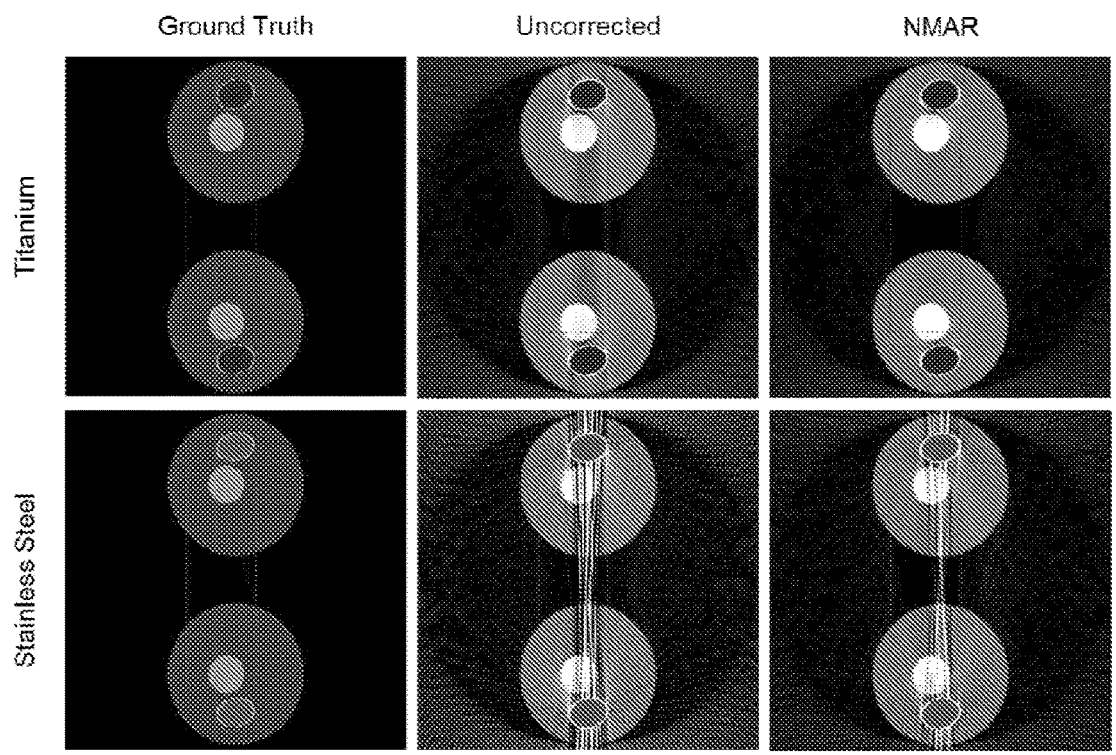
FIG. 18 shows six simulated test images showing the results of a normalization-based metal artifact reduction (NMAR) algorithm. The top-left and bottom-left images show the ground truth (70 keV mono-energetic image) for a titanium implant and a stainless steel implant, respectively. The top-middle and bottom-middle images show uncorrected versions (initial reconstruction from a 120 kVp scan) of the images of the top-left and bottom-left, respectively. The top-right and bottom-right images show the corrected reconstructed images of the top-middle and bottom-middle images, respectively, using an NMAR algorithm. The dotted box in each of these images outlines the streak region from which patches were extracted for network training.

FIG. 18 shows an example image of each case with the streak regions outlined by dotted boxes. From the full images, two million patches of size 32×32 were extracted from the streak regions to form the dataset for training the CNN. In FIG. 18, the top-left and bottom-left images show the ground truth (70 keV mono-energetic image) for a titanium implant and a stainless steel implant, respectively. The top-middle and bottom-middle images show uncorrected versions (initial reconstruction from a 120 kVp scan) of the images of the top-left and bottom-left, respectively. The top-right and bottom-right images show the corrected reconstructed images of the top-middle and bottom-middle images, respectively, using the NMAR algorithm.

Figure 19:
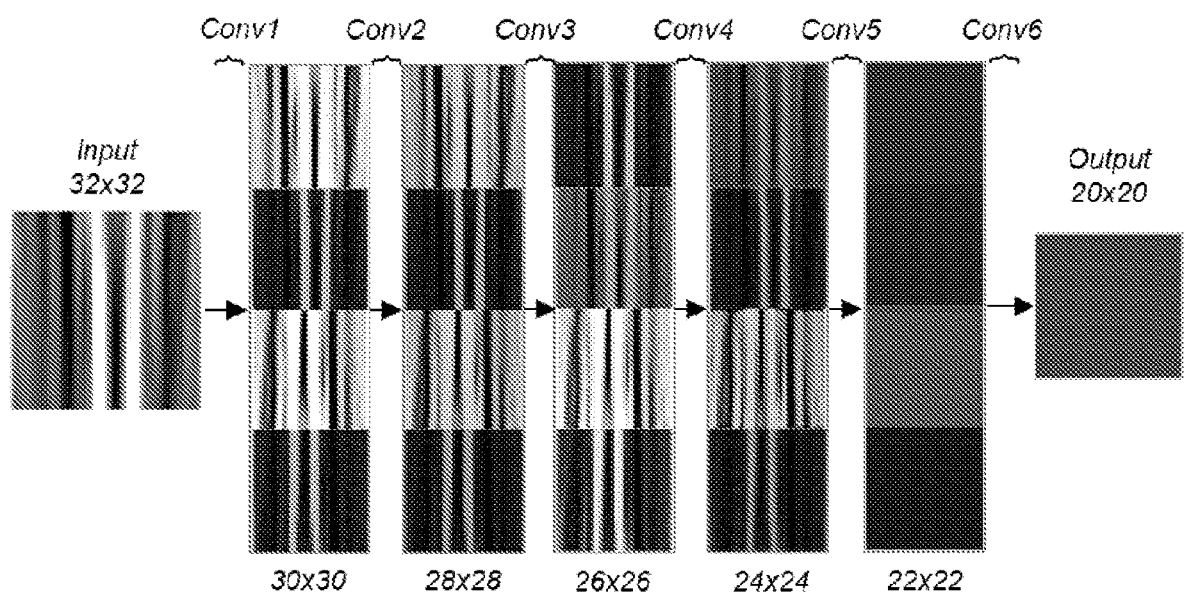
FIG. 19 shows a representation of a CNN containing six convolutional layers. Layers 1 through 5 have 32 filters and a 3×3 kernel, while the sixth layer has 1 filter and a 3×3 kernel. The first five layers are followed by a rectified linear unit for non-linearity. Features are extracted from a 32×32 input patch, and the output prediction from these features gives a 20×20 patch.

The network structure used was a simple CNN with six convolutional layers. The first five layers contained 32 filters and a 3×3 kernel to extract features from the input patch and map them to the target patch. Each of the layers was followed by a rectified linear unit (ReLU) to introduce non-linearity. The last layer sums the estimates with 1 filter and a 3×3 kernel to form the final output patch of size 20×20. FIG. 19 illustrates the network structure.

Training was completed in the Caffe framework (see Reference [91], which is incorporated by reference herein in its entirety). The base learning rate was 10-4 with a reduction factor of 0.5 after every 50,000 iterations. One million training iterations were carried out to minimize the loss, which is the mean squared error between the input and the target patch for each training iteration (batch size of 50).

Figure 20:
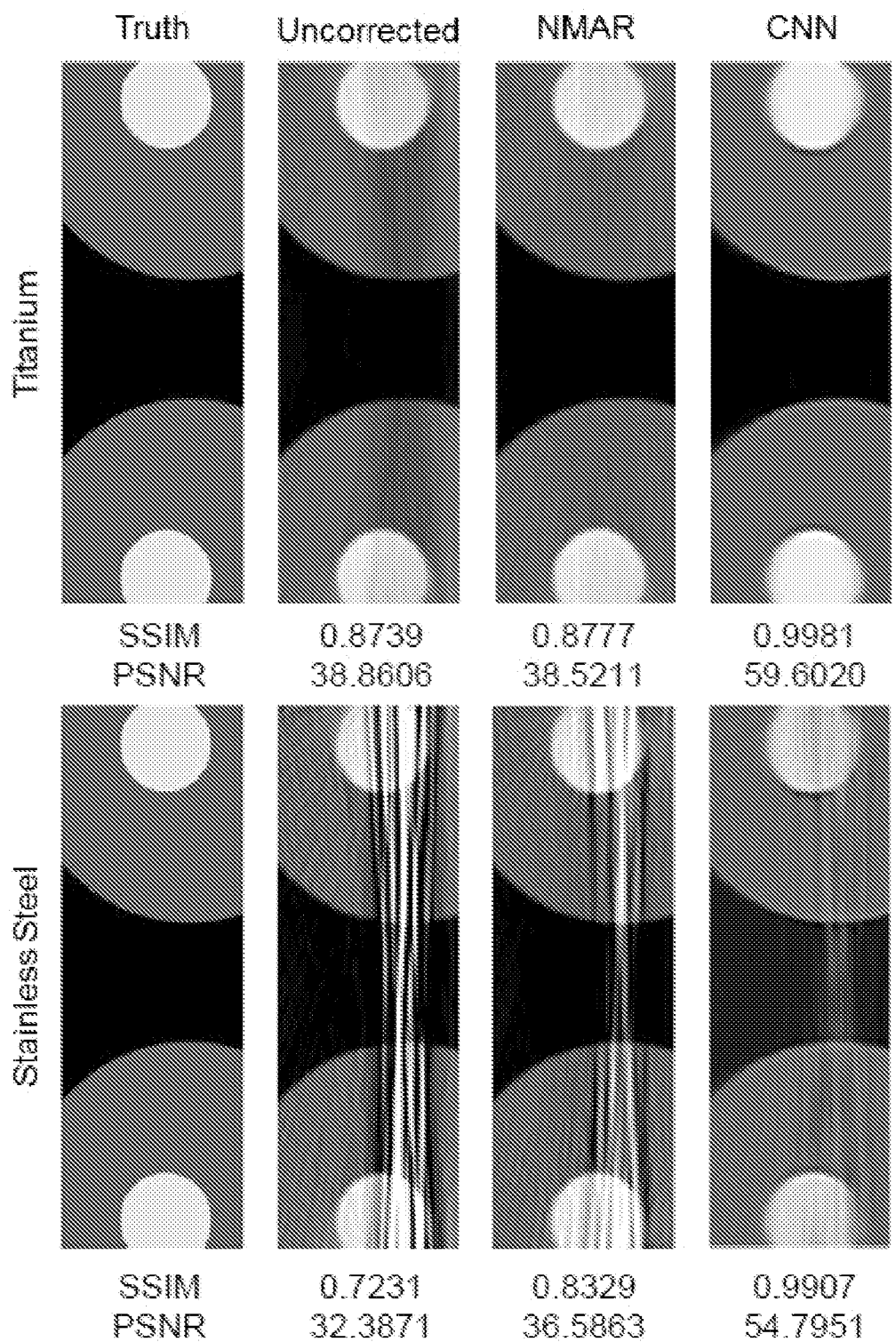
FIG. 20 shows results for the streak regions from FIG. 18, with the corresponding image quality metrics in reference to the ground truth shown underneath (SSIM is the structural similarity index, and PSNR is the peak signal-to-noise ratio). The top row shows the streak region for the titanium implant, and the bottom row shows the streak region for the stainless steel implant from FIG. 18. The first column is the ground truth, the second column is the uncorrected, and the third column is for the reconstructed image using NMAR. The fourth column shows the results after using deep learning with a CNN to reconstruct the image. The NMAR image was used as the input to the CNN, giving MAR results better than any related art reconstruction methods.

The network performance was tested using patches from the streak regions (dotted boxes) in FIG. 18. The NMAR corrected images served as the input to the CNN, and the forward prediction process mapped the input to the ground truth. The ground truth and input streak regions extracted from FIG. 18 are shown in FIG. 20 for the representative titanium and stainless steel cases. In FIG. 20, the top row shows the streak region for the titanium implant, and the bottom row shows the streak region for the stainless steel implant from FIG. 18. The first column is the ground truth, the second column is the uncorrected, and the third column is for the reconstructed image using NMAR. The fourth column shows the results after using deep learning with a CNN to reconstruct the image. The NMAR image was used as the input to the CNN, giving MAR results better than any related art reconstruction methods.

Referring to FIG. 20, the CNN prediction significantly reduced streaking artifacts for both types of metal implants. It can be observed that the titanium case was mapped well to the ground truth, given that the input contained much less severe streaks than the stainless steel case. For stainless steel, although artifacts remained, the CNN still recovered much of the underlying background. Quantitative analysis showed that the CNN yielded substantially higher image quality than NMAR alone as measured by structural similarity index (SSIM) and peak signal-to-noise ratios (PSNR).

The results demonstrate that deep learning is a good way to correct metal artifacts in CT images, and this improvement is in addition to the state of the art performance achieved using any existing approach. The CNN combined with the state-of-the-art NMAR algorithm to provide substantial reduction of streaks in critical image regions. Visually, the best results were achieved for titanium implant cases. Titanium produces less severe artifacts than stainless steel, and the network has an easier path to achieving effective correction. In the case of stainless steel implants, the streaks were more severe, and the CNN prediction still corrected for residual artifacts, though less effectively than with titanium. Deep learning can have an important role in achieving better image quality for MAR and other specific CT tasks, and in particular may enable more accurate tumor volume estimation for proton therapy planning.

Example 7

Numerical simulations were performed to demonstrate the feasibility and merits of deep-learning-based sinogram completion for MAR according to an embodiment of the subject invention. The sinograms used as training and validation data were generated using the Radon transform (i.e., simple line-integrals in a parallel-beam configuration) of simulated 2D objects including superimposed ellipses with random orientation, size, aspect-ratio, and attenuation. For simplicity, the trace of the metal was assumed to be a band of constant width at the center of the detector, as would be created by a circular metal object at the center of the image region. In the sinograms shown, the metal trace corresponds to a horizontal band in the sinogram. Consequently, a central circular region in the original simulated image is replaced with the local mean value (with a smooth transition at the edges of the circular region) prior to creating the simulated projection data that was used for training. In this manner the projection data was avoided in the missing data region to contain image information that is due to structures that are located in the metal region of the object (and which therefore should not be used for training).

Images were created with a size of 511×511 voxels, and a sinogram was created for view angles spanning 360 degrees, with a 0.5 degree separation between projections, resulting in a sinogram consisting of 720 views. The images contained a simulated circular metal region of diameter 45 voxels at the center of the image, and the missing data region in the resultant sinogram corresponded to a (horizontal) band of 45 detector channels. Image simulation as well as creation of projection data and reconstructed images was performed using Matlab's radon and iradon functions.

Figure 21:
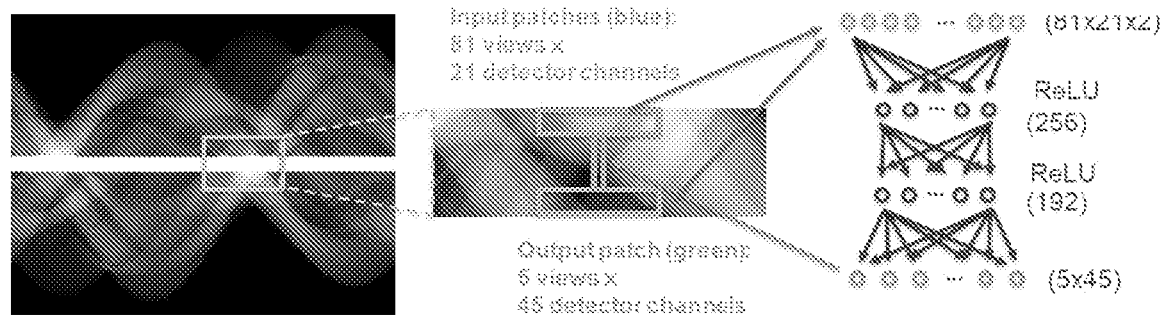
FIG. 21 shows three images demonstrating MAR using deep learning according to an embodiment of the subject invention. The left image is an example sinogram with a metal trace shown as a white horizontal band at the center. The middle image shows an enlarged view of the region of interest (ROI) identified with the box in the left image, with the top and bottom rectangles of the middle image being the input patches of the deep learning network (labeled as "blue" in the figure) and the middle rectangle of the middle image being the output patch of the deep learning network (labeled as "green" in the figure). The right portion of FIG. 21 shows a diagram of the architecture of the network used, with two hidden layers.

The deep learning network took as input two patches of size 81×21 in the sinogram, with one patch located on either side (top and bottom) of the missing data region. Each patch corresponded to an interval of 21 detector channels adjacent to the missing data interval on the detector, covering an angular range of +/−20 degrees relative to the considered view angle (i.e., from 40 views before to 40 views after the currently considered view angle). The corresponding output patch corresponded to an interval of 5 views (from two before to two after the current view angle), spanning the entire height of the metal trace (i.e., 45 detector channels). This geometry is illustrated in FIG. 21, where a sinogram is shown (left), with a metal trace indicated by the horizontal white bar across the sinogram. A ROI of the sinogram (enlarged) is also shown in the middle (lateral) section of FIG. 21, with the top and bottom rectangles of the middle image being the input patches of the deep learning network (labeled as "blue" in the figure) and the middle rectangle of the middle image being the output patch of the deep learning network (labeled as "green" in the figure). The right portion of FIG. 21 shows a diagram of the architecture of the network used, with two hidden layers. In the first layer a set of 256 features (each corresponding to an analysis filter of size 81×21×2) was extracted, which was then mapped to a set of 192 features, where each of those mapped features was then propagated to the target patch in the missing data domain by using a 5×45 "synthesis" patch. With the exception of the last layer, each layer used a ReLU (rectifying linear unit) non-linearity.

The training of the network was based on about 30,000 datasets that were extracted from a set of 500 simulated objects and the associated sinograms. For evaluation, interpolated sinograms were generated from individual patch-based estimates by creating an estimate for each single view angle (using the trained deep learning network), and then performing a simple averaging of the resulting overlapping output patches.

Figure 22:
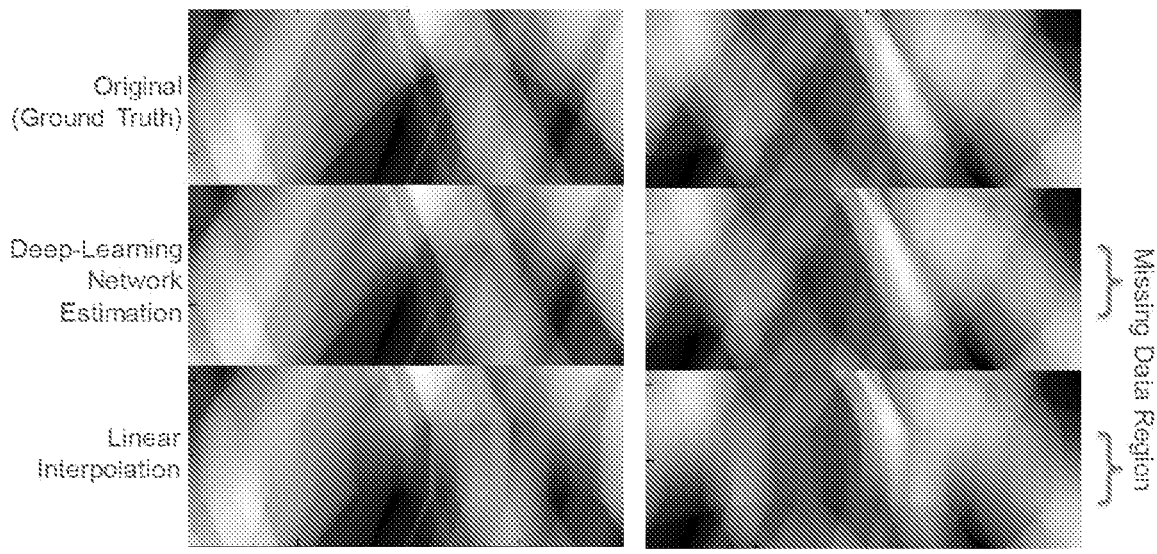
FIG. 22 shows six images example ROIs of two sonograms (one sinogram in each column). The first row shows a central section of the original (ground truth) sinogram, the second row shows the corresponding estimated (by deep learning) sinogram, and the bottom row shows the sinogram with linear interpolation of the metal trace region for comparison. Each image has a height of 87 pixels and contains the metal trace (horizontal band with a height of 45 pixels) at the center thereof, and the adjacent bands (of 21 pixel height each) on which the estimation is based immediately above and below. The interpolation using the deep learning network performed much better in capturing and representing the sinusoidal character of the traces due to the structures of the imaged object.

FIG. 22 shows results of ROIs of interpolated sinograms (one in each column). The first row shows a central section of the original (ground truth) sinogram, the second row shows the corresponding estimated (by deep learning) sinogram, and the bottom row shows the sinogram with linear interpolation of the metal trace region for comparison. Each image has a height of 87 pixels and contains the metal trace (horizontal band with a height of 45 pixels) at the center thereof, and the adjacent bands (of 21 pixel height each) on which the estimation is based immediately above and below. Referring to FIG. 21, the interpolation using the deep learning network performed much better in capturing and representing the sinusoidal character of the traces due to the structures of the imaged object. In particular, the sinogram interpolation created with the deep learning network achieved a much better "blending" with the adjacent known data bands, and was clearly superior in capturing and representing the characteristics of the data consisting of "superimposed sinusoidal traces".

Figure 23A:
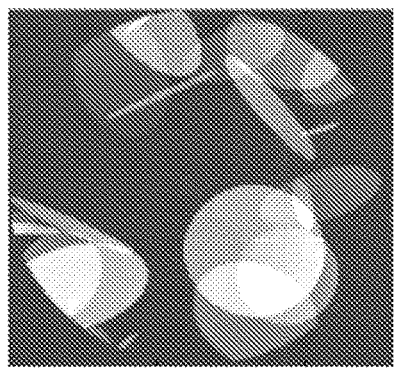
FIGS. 23A-23E show images demonstrating image reconstruction with deep learning.
Figure 23B:
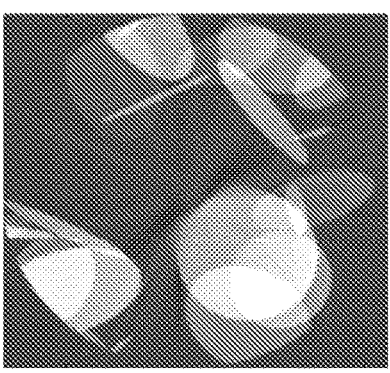
Figure 23C:
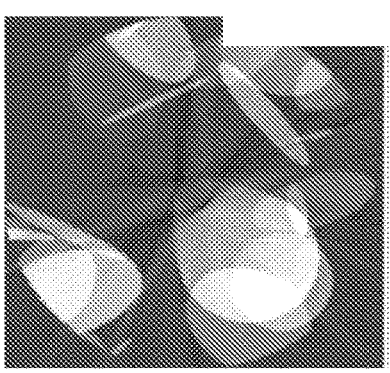
Figure 23D:
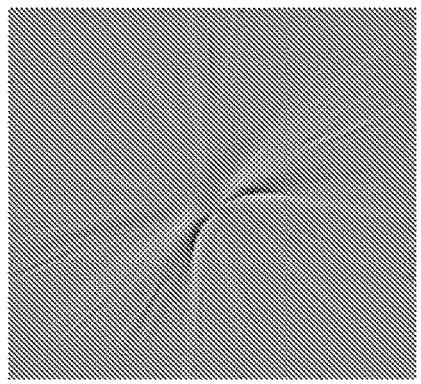
Figure 23E:
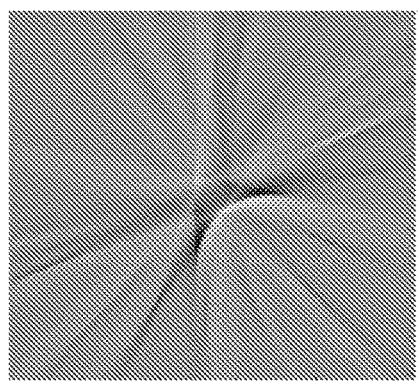

In addition, for sinograms interpolated with our deep learning approach the reconstructed image was reconstructed. For reference, the original image and a reconstruction obtained from a sinogram interpolated with simple view-by-view linear interpolation are also shown. These results are shown in FIGS. 23A-23E. FIG. 23A shows the original image; FIG. 23B shows the image of FIG. 23A reconstructed by deep learning interpolation of a metal trace region; and FIG. 23C shows the image of FIG. 23A reconstructed by linear interpolation of a metal trace region. FIG. 23D shows the difference between the reconstruction of FIG. 23B (deep learning) and the original image of FIG. 23A; and FIG. 23E shows the difference between the reconstruction of FIG. 23C (linear interpolation) and the original image of FIG. 23A. Referring to FIGS. 23A-23E, the deep learning reconstruction leads to clear improvement of banding and streaking artifacts, corresponding to a root mean square (RMS) error improvement of 37%. The remaining artifacts in the result obtained with the deep learning were predominantly of a high-frequency nature, which may be due to the relatively small number of layers and neurons in the network used.

The results of the simulation demonstrate the potential of deep learning techniques to achieve good performance in addressing streak and banding artifacts due to metal in the field of view, with potential applicability to other missing data scenarios (e.g., truncation). Increasing the number of layers in the neural network could drastically improve performance (even when the total number of neurons is decreased).

Example 8

In order to train a CNN, CatSim was used to generate dual-energy sinograms as input images from ground truth images and their corresponding mono-energetic sinograms. CatSim is a simulation environment for X-ray CT developed by GE. First, generate 1,000 Shepp-Logan-type phantoms were generated, which included a pseudorandom number of ellipses. For each phantom, three projection images were simulated using tube voltages of 80 kVp and 120 kVp, as well as a mono-energetic X-ray source of 100 keV, respectively. Each of the resulting 3,000 images was of size 200×200. Each image was then partitioned into overlapping 32×32 image patches, and datasets were obtained including 100,000 image patches for 120 kVp, 80 kVp, and 100 keV sinograms, respectively.

After these ground truth images were obtained, the structure of the CNN could be designed. Unlike many applications in image classification, where the label of the network is defined to be a vector with each component being the score for each class, here each label was defined to be a ground truth mono-energetic sinogram corresponding to the phantom of the input images. Another difference between the CNN architecture according to an embodiment of the subject invention and a typical CNN used for classification is that there is no pooling layer in the network according to an embodiment of the subject invention. The CNN according to an embodiment of the subject invention can include 10 layers, including 5 convolutional layers, 4 (Rectified Linear Unit) ReLU layers, and one last loss layer. The size of the network input can be regarded as 32×32×2 because there is a pair of image patches from dual-energy data. The first convolutional layer has 32 filters with kernel size 5×5×2, and pad 2. The second convolutional layer has 32 filters with size 3×3×32 and pad 1. The third layer has 32 filters with size 1×7×32 and pad size 0×0×3×3. The fourth layer has 32 filters with size 7×1×32 and pad 3×3×0×0, and the last layer has 1 filter with size 3×3×32, pad 1. The key in choosing these parameters is to make sure the resulting feature map after the first 9 layers must be of size 32×32×1, which is a prediction about mono-energetic image patch at 100 keV. During the training process, the parameters of the network were updated by stochastic gradient descent (SGD). The learning rate in SGD determines the speed of convergence and the optimality of the solution, and it also depends on the batch size. In the simulations, batch size 32 was used, and the performance of different learning rates ranging from 0.0001 to 0.001 was compared.

Figure 13:
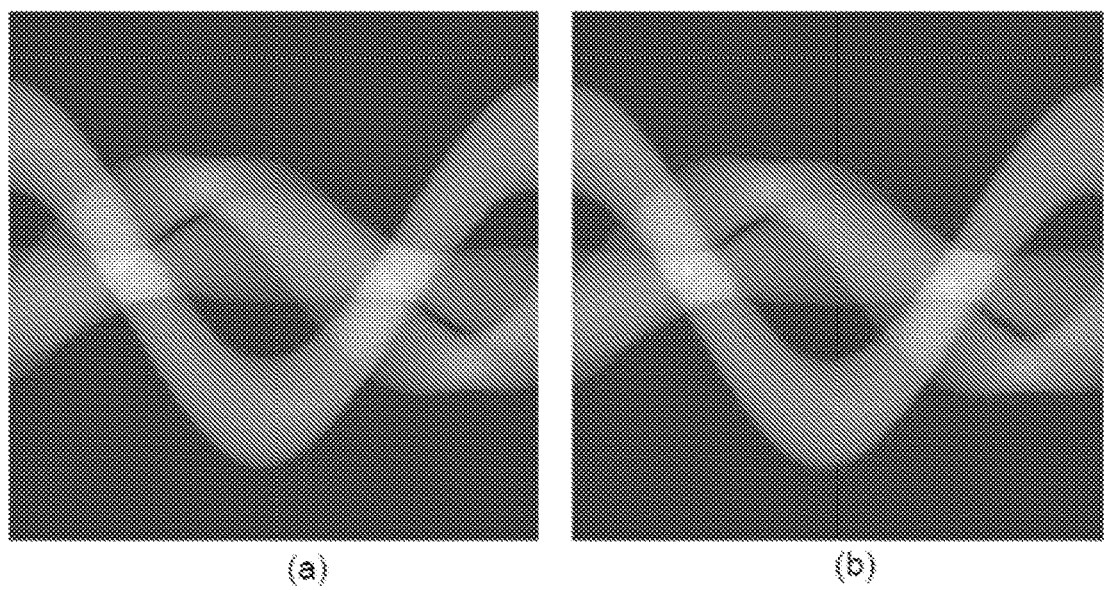
FIGS. 13A and 13B show the results of mono-energetic sinograms generated from dual-energy CT sinograms using a CNN.

Input datasets (dual-energy CT images) with size 32×32×2×100000 were used, and their corresponding labels (ground truth mono-energetic images) of size 32×32×1×100000 were used to train the CNN. Size of the feature map after the 9th layer (the layer before the last loss layer) in the forward propagation is the same as the size of labels. The loss function is $l_1$ norm. The training process is via the minimization of the loss function. In the simulations, the same epoch was chosen, which is the number of full training cycles, such that the loss function almost stops decreasing through iterations. To evaluate the performance of the network, the last loss layer was eliminated after training, a few pairs of 32×32 image patches from both training set and test set was used to obtain the output of the trained CNN, and the results were compared with the expected outputs from label set. Because the ultimate goal is to generate the full size 200×200 mono-energetic sinograms, the performance was also tested by using a pair of 200×200 dual-energy images as input and the CNN output and ground truth image was compared. The resultant mono-energetic sinograms were quite accurate compared with the ground truth mono-energetic sinograms, as shown in FIGS. 13A (ground truth) and 13B (output from the CNN).

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. H. Greenspan, B. V. Ginneken, and R. M. Summers, "Guest editorial deep learning in medical imaging: Overview and future promise of an exciting new technique," IEEE Trans. Med. Imag., vol. 35, no. 5, pp. 1153-1159, March 2016.
2. R. D. Hof, 10 Breakthrough Technologies—Deep Learning. Cambridge, Mass., USA: MIT Technology Review, 2013.
3. J. H. Byrne, R. Heidelberger, and M. N. Waxham, From Molecules to Networks: An Introduction to Cellular and Molecular Neuroscience, 3rd ed. Boston, Mass., USA: Academic, 2014.
4. M. Anthony and P. L. Bartlett, Neural Network Learning: Theoretical Foundations. New York, N.Y., USA: Cambridge Univ. Press, 1999.
5. G. E. Hinton, S. Osindero, and Y.-W. Teh, "A fast learning algorithm for deep belief nets," Neural Comput., vol. 18, no. 7, pp. 1527-1554, July 2006.
6. D. Silver et al., "Mastering the game of go with deep neural networks and tree search," Nature, vol. 529, p. 484-489, January 2016.
7. Y. LeCun, Y. Bengio, and G. Hinton, "Deep learning," Nature, vol. 521, pp. 44-436, May 2015.
8. (Sep. 1, 2016). [Online]. Available: http://people.idsia.ch/Huergen/deep-learning-conspiracy.html
9. I. Goodfellow, Y. Bengio, and A. Courville, Deep Learning. Cambridge, Mass., USA: MIT Press, 2016.
10. S. K. Zhou, "Deep learning guide to MICCAI 2015," 18th Int. Conf. Med. Image Comput. Comput. Assisted Intervent., Munich, Germany, October 2015.
11. K. Hornik, M. Stinchcombe, and H. White, "Multilayer feedforward networks are universal approximators," Neural Netw., vol. 2, no. 5, pp. 359-366, 1989.
12. K. Hornik, "Approximation capabilities of multilayer feedforward networks," Neural Netw., vol. 4, no. 2, pp. 251-257, 1991.
13. A. C. Kak and M. Slaney, Principles of Computerized Tomographic Imaging. Philadelphia, Pa., USA: SIAM, 2001.
14. A. Katsevich, "An improved exact filtered backprojection algorithm for spiral computed tomography," Adv. Appl. Math., vol. 32, no. 4, pp. 681-697, May 2004.
15. C. H. McCollough et al., "Achieving routine submillisievert CT scanning: Report from the summit on management of radiation dose in CT," Radiol-ogy, vol. 264, no. 2, pp. 567-580, August 2012.
16. J. Hsieh, Computed Tomography: Principles, Design, Artifacts, and Recent Advances, 2nd ed. Hoboken, N.J., USA: Wiley, 2009.
17. L. L. Geyer et al., "State of the art: Iterative CT reconstruction techniques," Radiology, vol. 276, no. 2, pp. 338-356, August 2015.
18. E. C. Behrman, V. Chandrashekar, Z. Wang, C. K. Belur, J. E. Steck, and S. R. Skinner. (2002). "A quantum neural network computes entanglement." [Online]. Available: https://arxiv.org/abs/quant-ph/0202131.
19. The National Lung Screening Trial Research Team, "Reduced lung-cancer mortality with low-dose computed tomographic screening," New England J. Med., vol. 365, pp. 395-409, August 2011.
20. B. De Man et al., "CatSim: A new computer assisted tomography simulation environment," Proc. SPIE, vol. 6510, pp. U1191-U1198, March 2007.
21. Q. Yang et al., "Big data from CT scanning," JSM Biomed. Imag., vol. 2, no. 1, pp. 1003-1-1003-6, 2015.
22. M. J. Ackerman, "The visible human project," J. Biocommun., vol. 18, no. 2, p. 14, 1991.
23. X. G. Xu, V. Taranenko, J. Zhang, and C. Shi, "A boundary-representation method for designing wholebody radiation dosimetry models: Pregnant females at the ends of three gestational periods-RPI-P3, -P6 and -P9," Phys. Med. Biol., vol. 52, no. 23, pp. 7023-7044, December 2007.
24. B. Q. Huynh, H. Li, and M. Giger, "Digital mammographic tumor classification using transfer learning from deep convolutional neural networks," J. Med. Imag., vol. 3, no. 3, p. 034501, August 2016.
25. M. Chen, Y. Xi, W. Cong, B. Liu, B. Wei, and G. Wang, "X-ray CT geometrical calibration via locally linear embedding," J. X-Ray Sci. Technol., vol. 24, no. 2, pp. 241-256, March 2016.
26. G. Wang et al., "Vision 20/20: Simultaneous CT-MM—Next chap-ter of multimodality imaging," Med. Phys., vol. 42, pp. 5879-5889, October 2015.
27. S. Tan et al., "Tensor-based dictionary learning for dynamic tomo-graphic reconstruction," Phys. Med. Biol., vol. 60, no. 7, pp. 2803-2818, April 2015.
28. M. T. Munley, C. E. Floyd, Jr., J. E. Bowsher, and R. E. Coleman, "An artificial neural network approach to quantitative single photon emis-sion computed tomographic reconstruction with collimator, attenuation, and scatter compensation," Med. Phys., vol. 21, no. 12, pp. 1889-1899, December 1994.
29. J. P. Kerr and E. B. Bartlett, "Neural network reconstruction of single-photon emission computed tomography images," J. Digit. Imag., vol. 8, no. 3, pp. 116-126, August 1995.

30. S. Ravishankar and Y. Bresler, "MR image reconstruction from highly undersampled k-space data by dictionary learning," IEEE Trans. Med. Imag., vol. 30, no. 5, pp. 1028-1041, May 2011.
31. Q. Xu, H. Yu, X. Mou, L. Zhang, J. Hsieh, and G. Wang, "Low-dose X-ray CT reconstruction via dictionary learning," IEEE Trans. Med. Imag., vol. 31, no. 9, pp. 1682-1697, September 2012.
32. S. Wang et al., "Accelerating magnetic resonance imaging via deep learning," presented at the IEEE 13th Int. Symp. Biomed. Imag., April 2016, pp. 514-517.
33. K. Hammernik, F. Knoll, D. K. Sodickson, and T. Pock, "Learn-ing a variational model for compressed sensing MRI reconstruction," presented at the 24th Annu. Meeting Int. Soc. Magn. Reson. Med., 2016, pp. 331-332.
34. H. M. Zhang et al. (2016). "Image prediction for limited-angle tomography via deep learning with convolutional neural network." [Online]. Available: https://arxiv.org/abs/1607.08707.
35. K. Dabov, A. Foi, V. Katkovnik, and K. Egiazarian, "Image denois-ing with block-matching and 3D filtering," Proc. SPIE, vol. 6064, pp. 606414-1-12, February 2006.
36. H. Chen et al. (2016). "Low-dose CT denoising with convolutional neural network." [Online]. Available: https://arxiv.org/abs/1610.00321.
37. P. Mehta and D. J. Schwab. (2014). "An exact mapping between the variational renormalization group and deep learning." [Online]. Available: http://arxiv.org/abs/1410.3831.
38. C. Szegedy et al. (2014). "Intriguing properties of neural networks." [Online]. Available: https://arxiv.org/abs/1312.6199.
39. A. Nguyen, J. Yosinski, and J. Clune. (2015). "Deep neural networks are easily fooled: High confidence predictions for unrecognizable images." [Online]. Available: http://arxiv.org/pdf/1412.1897v2.pdf.
40. F. Natterer and F. Wiibbeling, Mathematical Methods in Image Reconstruction. Philadelphia, Pa., USA: SIAM, 2001.
41. G. T. Herman and R. Davidi, "Image reconstruction from a small num-ber of projections," Inverse Probl, vol. 24, no. 4, pp. 45011-45028, August 2008.
42. V. Estellers, J.-P. Thiran, and X. Bresson, "Enhanced compressed sensing recovery with level set normals," IEEE Trans. Image Process., vol. 22, no. 7, pp. 2611-2626, July 2013.
43. H. Jaeger, "Artificial intelligence: Deep neural reasoning," Nature, vol. 538, pp. 467-468, October 2016.
44. T. S. Kuhn, The Structure of Scientific Revolutions. Chicago, Ill., USA: Univ. Chicago Press, 1962.
45. J. Preston and T. S. Kuhn, The Structure of Scientific Revolutions: A Reader's Guide. New York, N.Y., USA: Continuum, 2008.
46. A. J. G. Hey, The Fourth Paradigm: Data-Intensive Scientific Discovery, accessed on Sep. 1, 2016. [Online]. Available: http://202.120.81.220:81/inter/uploads/readings/four-paradigm .pdf.
47. A. Shademan, R. S. Decker, J. D. Opfermann, S. Leonard, A. Krieger, and P. C. W. Kim, "Supervised autonomous robotic soft tissue surgery," Sci. Transl. Med., vol. 8, no. 337, p. 337ra64, May 2016.
48. accessed on Sep. 1, 2016 [Online]. Available: https://www.4catalyzer.com/49.
49. accessed on Sep. 1, 2016. [Online]. Available: http://www.nanalyze.com/2016/02/enlitic-deep-learning-algorithms-for-medical-imaging/50.
50. Krizhevsky A, Sutskever I, Hinton G. 2012 ImageNet classification with deep convolutional neural networks. In Proc. 26th Annual Conf. on Neural Information Processing Systems, Lake Tahoe, Nev., 3-6 Dec. 2012, pp. 1090-1098.
51. Hinton G et al. 2012 Deep neural networks for acoustic modeling in speech recognition. IEEE Signal Process. Mag. 29, 82-97.
52. Yann LeCun, Yoshua Bengio & Geoffrey Hinton, Deep learning, Nature 521, 436-444 (28 May 2015).
53. Wang, G. "A Perspective on Deep Imaging", IEEE Access, vol 4., November 2016.
54. Gjesteby, L., De Man, B., Jin, Y., Paganetti, H., Verburg, J., Giantsoudi, D., Wang, G., Metal Artifacrt Reduction in CT: Where Are We After Four Decades?, IEEE Access, vol. 4, 2016.
55. J. Y. Huang et al., "An evaluation of three commercially available metal artifact reduction methods for CT imaging," Phys. Med. Biol., vol. 60, no. 3, p. 1047, 2015.
56. Wagenaar D, van der Graaf E R, van der Schaaf A, Greuter M J W (2015) Quantitative Comparison of Commercial and Non-Commercial Metal Artifact Reduction Techniques in Computed Tomography. PLoS ONE 10(6), 2015.
57. J. Müller and T. M. Buzug, "Spurious structures created by interpolationbased CT metal artifact reduction," in Proc. SPIE 7258, Med. Imag., Phys. Med. Imag., March 2009.
58. Kalender W. et al. "Reduction of CT artifacts caused by metallic impants." Radiology, 1987.
59. Glover G. and Pelc N. "An algorithm for the reduction of metal clip artifacts in CT reconstructions." Med. Phys., 1981.
60. Mahnken A. et al, "A new algorithm for metal artifact reduction in computed tomogrpaby, In vitro and in vivo evaluation after total hip replacement." Investigative Radiology, vol. 38, no. 12, pp. 769-775, December 2003.
61. Meyer E, Raupach R, Lell M, Schmidt B, Kachelriess M., Normalized metal artifact reduction (NMAR) in computed tomography. Med Phys. 2010 October; 37(10): 5482-93.
62. Boas F E, Fleischmann D., Evaluation of two iterative techniques for reducing metal artifacts in computed tomography. Radiology. 2011 June; 259(3):894-902.
63. Meyer E, Raupach R, Lell M, Schmidt B, Kachelrie B M. Frequency split metal artifact reduction (FSMAR) in computed tomography. Med Phys. 2012; 39: 1904-16.
64. Dong C., Loy C. C., He, K., Tang, X., Image Super-Resolution Using Deep Convolutional Networks, IEEE Trans. PAMI, 38(2), 295-307, 2016.
65. Kim, J., Lee, J. K., and Lee, K. M., Accurate Image Super-Resolution Using Very Deep Convolutional Networks, IEEE CVPR2016, 1646-1654.
66. L. Gjesteby, B. De Man, Y. Jin, H. Paganetti, J. Verburg, D. Giantsoudi, and G. Wang, "Metal Artifact Reduction in CT: Where Are We After Four Decades?," *IEEE Access*, vol. 4, pp. 5826-5849, 2016.
67. G. X. Ding and W. Y. Christine, "A study on beams passing through hip prosthesis for pelvic radiation treatment," *Int. J. Radiat. Oncol. Biol. Phys.*, vol. 51, no. 4, pp. 1167-1175, 2001.
68. C. Reft, R. Alecu, I. J. Das, B. J. Gerbi, P. Keall, E. Lief, B. J. Mijnheer, N. Papanikolaou, C. Sibata, and J. Van Dyk, "Dosimetric considerations for patients with HIP prostheses undergoing pelvic irradiation. Report of the AAPM Radiation Therapy Committee Task Group 63," *Med. Phys.*, vol. 30, no. 6, pp. 1162-1182, 2003.

69. R. M. Lewitt and R. H. T. Bates, "Image-reconstruction from projections. III. Projection completion methods (theory)," *Optik (Stuttg).*, vol. 50, no. 3, pp. 189-204, 1978.
70. T. Hinderling, P. Ruegsegger, M. Anliker, and C. Dietschi, "Computed Tomography Reconstruction from Hollow Projections: An Application to In Vivo Evaluation of Artificial Hip Joints," *J. Comput. Assist. Tomogr.*, vol. 3, no. 1, pp. 52-57, 1979.
71. G. H. Glover and N. J. Pelc, "An algorithm for the reduction of metal clip artifacts in CT reconstructions.," *Med. Phys.*, vol. 8, no. 6, pp. 799-807, 1981.
72. W. A. Kalender, R. Hebel, and J. Ebersberger, "Reduction of CT artifacts caused by metallic implants," *Radiology*, vol. 164, no. 2, pp. 576-577, 1987.
73. C. R. Crawford, J. G. Colsher, N. J. Pelc, and A. H. R. Lonn, "High speed reprojection and its applications," in *SPIE Medical Imaging II,* 1988, pp. 311-318.
74. R. Naidu, I. Bechwati, S. Karimi, S. Simanovsky, and C. Crawford,
75. "Method of and system for reducing metal artifacts in images generated by x-ray scanning devices," U.S. Pat. No. 6,721,387 B1, 2004.
76. C. S. Olive, M. R. Klaus, V. Pekar, K. Eck, and L. Spies, "Segmentation aided adaptive filtering for metal artifact reduction in radio-therapeutic CT images," in *SPIE Medical Imaging* 2004, 2004, vol. 5370, pp. 1991-2002.
77. C. Lemmens, D. Faul, and J. Nuyts, "Suppression of metal artifacts in CT using a reconstruction procedure that combines MAP and projection completion," *IEEE Trans. Med. Imaging*, vol. 28, no. 2, pp. 250-60, 2009.
78. J. Müller and T. M. Buzug, "Spurious structures created by interpolationbased CT metal artifact reduction," in *SPIE Medical Imaging,* 2009, p. 72581Y-72581Y.
79. E. Meyer, F. Bergner, R. Raupach, T. Flohr, and M. Kachelrie B, "Normalized metal artifact reduction (NMAR) in computed tomography," *Med. Phys.*, vol. 37, no. 10, pp. 5482-5493, 2010.
80. E. Meyer, R. Raupach, B. Schmidt, A. H. Mahnken, and M. Kachelriess, "Adaptive Normalized Metal Artifact Reduction (ANMAR) in Computed Tomography," in 2011 *IEEE Nuclear Science Symposium Conference Record,* 2011, pp. 2560-2565.
81. G. Henrich, "A simple computational method for reducing streak artifacts in CT images," *Comput. Tomogr.*, vol. 4, no. 1, pp. 67-71, 1980.
82. M. Bal, H. Celik, K. Subramanyan, K. Eck, and L. Spies, "A radial adaptive filter for metal artifact reduction," in *SPIE Medical Imaging* 2005, 2005, vol. 5747, pp. 2075-2082.
83. O. Watzke and W. A. Kalender, "A pragmatic approach to metal artifact reduction in CT: Merging of metal artifact reduced images," *Eur. Radiol.*, vol. 14, no. 5, pp. 849-856, 2004.
84. Y. LeCun, Y. Bengio, and G. Hinton, "Deep learning," *Nature*, vol.
85. 521, no. 7553, pp. 436-444, May 2015.
86. Y. LeCun, B. Boser, J. S. Denker, D. Henderson, R. E. Howard, W. Hubbard, and L. D. Jackel, "Backpropagation applied to handwritten zip code recognition," *Neural Comput.*, vol. 1, no. 4, pp. 541-551, 1989.
87. A. Krizhevsky, I. Sutskever, and G. E. Hinton, "Imagenet classification with deep convolutional neural networks," in *Advances in neural information processing systems,* 2012, pp. 1097-1105.
88. C. Szegedy, W. Liu, Y. Jia, P. Sermanet, S. Reed, D. Anguelov, D. Erhan, V. Vanhoucke, and A. Rabinovich, "Going deeper with convolutions," in *Proceedings of the IEEE Conference on Computer Vision and Pattern Recognition,* 2015, pp. 1-9.
89. B. De Man, S. Basu, N. Chandra, B. Dunham, P. Edic, M. Iatrou, S. McOlash, P. Sainath, C. Shaughnessy, and B. Tower, "CatSim: a new computer assisted tomography simulation environment," in *Medical Imaging,* 2007, p. 65102G-65102G.
90. C. Dong, C. C. Loy, K. He, and X. Tang, "Image super-resolution using deep convolutional networks," *IEEE Trans. Pattern Anal. Mach. Intell.*, vol. 38, no. 2, pp. 295-307, 2016.
91. Y. Jia, E. Shelhamer, J. Donahue, S. Karayev, J. Long, R. Girshick, S. Guadarrama, and T. Darrell, "Caffe: Convolutional architecture for fast feature embedding," in *Proceedings of the 22nd ACM international conference on Multimedia,* 2014, pp. 675-678.
92. N. Haramati, R. B. Staron, K. Mazel-Sperling, K. Freeman, E. L. Nickoloff, C. Barax, and F. Feldman, "CT scans through metal scanning technique versus hardware composition," *Comput. Med. Imaging Graph.*, vol. 18, no. 6, pp. 429-434, 1994.
93. K. He, X. Zhang, S. Ren, and J. Sun, "Deep residual learning for image recognition," in *Proceedings of the IEEE Conference on Computer Vision and Pattern Recognition,* 2016, pp. 770-778.
94. D. J. Brenner and E. J. Hall, "Computed tomography—An increasing source of radiation exposure," New Eng. J. Med., vol. 357, pp. 2277-2284, 2007.
95. E. Y. Sidky and X. Pan, "Image reconstruction in circular cone-beam computed tomography by constrained, total-variation minimization," Phys. Med. Biol., vol. 53, no. 17, pp. 4777-4807, 2008.
96. Y. Zhang, Y, Wang, W. Zhang, et al., "Statistical iterative reconstruction using adaptive fractional order regularization," Biomed. Opt. Express, vol. 7, no. 3, pp. 1015-1029, 2016.
97. Y. Zhang, W. Zhang, Y. Lei, and J. Zhou, "Few-view image reconstruction with fractional-order total variation," J. Opt. Soc. Am. A, vol. 31, no. 5, pp. 981-995, 2014.
98. Y. Zhang, W.-H. Zhang, H. Chen, M.-L. Yang, T.-Y. Li, and J.-L. Zhou, "Few-view image reconstruction combining total variation and a high-order norm," Int. J. Imaging Syst. Technol., vol. 23, no. 3, pp. 249-255, 2013.
99. J. Ma, H. Zhang, Y. Gao et al., "Iterative image reconstruction for cerebral perfusion CT using a pre-contrast scan induced edge-preserving prior," Phys. Med. Biol., vol. 57, no. 22, pp. 7519-7542, 2012.
100. Y. Chen, Z. Yang, Y, Hu et al., "Thoracic low-dose CT image processing using an artifact suppressed large-scale nonlocal means," Phys. Med. Biol., vol. 57, no. 9, pp. 2667-2688, 2012.
101. Q. Xu, H. Yu, X. Mou, et al., "Low-dose x-ray CT reconstruction via dictionary learning," IEEE Trans. Med. Imaging, vol. 31, no. 9, pp. 1682-1697, 2012.
102. Y. Chen, X. Yin, L. Shi, et al., "Improving abdomen tumor low-dose CT images using a fast dictionary learning based processing," Phys. Med. Biol., vol. 58, no. 16, pp. 5803-5820, 2013.
103. K. Sheng, S. Gou, J. Wu, et al., "Denoised and texture enhanced MVCT to improve soft tissue conspicuity," Med. Phys., vol. 41, no. 10, 101916, 2014.
104. Y. LeCun, Y, Bengio and G. Hinton, "Deep learning," Nature, vol. 521, no. 7553, pp. 436-444, 2015.

105. S. Wang, Z. Su, L. Ying, et al., "Accelerating magnetic resonance imaging via deep learning," 2016 IEEE 13th International Symposium on Biomedical Imaging (ISBI), pp. 514-517, 2016.
106. H, Zhang, L. Li, K. Qiao, et al., "Image predication for limited-angle tomography via deep learning with convolutional neural network," arXiv:1607.08707, 2016.
107. Wang G, Perspective on deep imaging. IEEE Access, DOI: 10.1109/ACCESS.2016.2624938, 2016. (http://ieeexplore.ieee.org/document/7733110).
108. N. L. S. T. R. Team et al., "Reduced lung-cancer mortality with low-dose computed tomographic screening," *The New England Journal of Medicine*, vol. 2011, no. 365, pp. 395-409, 2011.
109. H. J. Aerts, E. R. Velazquez, R. T. Leijenaar, C. Parmar, P. Grossmann, S. Carvalho, J. Bussink, R. Monshouwer, B. Haibe-Kains, D. Rietveld et al., "Decoding tumour phenotype by noninvasive imaging using a quantitative radiomics approach," *Nature Communications*, vol. 5, 2014.
110. F. Han, G. Zhang, H. Wang, B. Song, H. Lu, D. Zhao, H. Zhao, and Z. Liang, "A texture feature analysis for diagnosis of pulmonary nodules using LIDC-IDRI database," in *International Conference on Medical Imaging Physics and Engineering*. IEEE, 2013, pp. 14-18.
111. W. Shen, M. Zhou, F. Yang, C. Yang, and J. Tian, "Multi-scale convolutional neural networks for lung nodule classification," in *International Conference on Information Processing in Medical Imaging*. Springer, 2015, pp. 588-599.
112. D. Kumar, A. Wong, and D. A. Clausi, "Lung nodule classification using deep features in CT images," in *12th Conference on Computer and Robot Vision*. IEEE, 2015, pp. 133-138.
113. T. Ojala, M. Pietikainen, and T. Maenpaa, "Multiresolution gray-scale and rotation invariant texture classification with local binary patterns," *IEEE Transactions on Pattern Analysis and Machine Intelligence*, vol. 24, no. 7, pp. 971-987, 2002.
114. N. Dalal and B. Triggs, "Histograms of oriented gradients for human detection," in *IEEE Computer Society Conference on Computer Vision and Pattern Recognition*, vol. 1. IEEE, 2005, pp. 886-893.
115. A. Krizhevsky, I. Sutskever, and G. E. Hinton, "ImageNet classification with deep convolutional neural networks," in *Advances in Neural Information Processing Systems*, 2012, pp. 1097-1105.
116. C. Szegedy, W. Liu, Y. Jia, P. Sermanet, S. Reed, D. Anguelov, D. Erhan, V. Vanhoucke, and A. Rabinovich, "Going deeper with convolutions," in *Proceedings of the IEEE Conference on Computer Vision and Pattern Recognition*, 2015, pp. 1-9.
117. K. He, X. Zhang, S. Ren, and J. Sun, "Deep residual learning for image recognition," in *Proceedings of the IEEE Conference on Computer Vision and Pattern Recognition*, 2016, pp. 770-778.
118. J. Yosinski, J. Clune, Y. Bengio, and H. Lipson, "How transferable are features in deep neural networks?" in *Advances in Neural Information Processing Systems*, 2014, pp. 3320-3328.
119. S. G. Armato III, G. McLennan, L. Bidaut, M. F. McNitt-Gray, C. R. Meyer, A. P. Reeves, B. Zhao, D. R. Aberle, C. I. Henschke, E. A. Hoffman et al., "The lung image database consortium (LIDC) and image database resource initiative (IDRI): a completed reference database of lung nodules on CT scans," *Medical physics*, vol. 38, no. 2, pp. 915-931, 2011.
120. A. Sharif Razavian, H. Azizpour, J. Sullivan, and S. Carlsson, "CNN features off-the-shelf: An astounding baseline for recognition," in *Pro-ceedings of the IEEE Conference on Computer Vision and Pattern Recognition Workshops*, 2014, pp. 806-813.
121. O. Russakovsky, J. Deng, H. Su, J. Krause, S. Satheesh, S. Ma, Z. Huang, A. Karpathy, A. Khosla, M. Bernstein et al., "ImageNet large scale visual recognition challenge," *International Journal of Computer Vision*, vol. 115, no. 3, pp. 211-252, 2015.
122. L. Breiman, "Random forests," *Machine Learning*, vol. 45, no. 1, pp. 5-32, 2001.
123. F. Pedregosa, G. Varoquaux, A. Gramfort, V. Michel, B. Thirion, O. Grisel, M. Blondel, P. Prettenhofer, R. Weiss, V. Dubourg et al., "Scikit-learn: Machine learning in python," *Journal of Machine Learning Research*, vol. 12, no. Oct, pp. 2825-2830, 2011.
124. S. Van der Walt, J. L. Schönberger, J. Nunez-Iglesias, F. Boulogne, J. D. Warner, N. Yager, E. Gouillart, and T. Yu, "Scikit-image: Image processing in python," *PeerJ*, vol. 2, p. e453, 2014.
125. Wang et al., International Patent Application Publication No. WO2014/176328.
126. Wang et al., U.S. Pat. No. 8,862,206.
127. Wang et al., U.S. Pat. No. 8,811,700.
128. Wang et al., U.S. Patent Application Publication No. 2011/0105880.
129. Wang et al., U.S. Pat. No. 7,697,658.
130. Wang et al., International Patent Application Publication No. WO2016/106348.
131. Wang et al., U.S. Patent Application Publication No. 2015/0157286.
132. Wang et al., U.S. Patent Application Publication No. 2015/0170361.
133. Wang et al., U.S. Patent Application Publication No. 2015/0193927.
134. Wang et al., International Patent Application Publication No. WO2015/164405.
135. Wang et al., U.S. Patent Application Publication No. 2016/0113602.
136. Wang et al., U.S. Patent Application Publication No. 2016/0135769.
137. Wang et al., U.S. Patent Application Publication No. 2016/0166852.
138. Wang et al., International Patent Application Publication No. WO2016/106348.
139. Wang et al., International Patent Application Publication No. WO2016/118960.
140. Wang et al., International Patent Application Publication No. WO2016/154136.
141. Wang et al., International Patent Application Publication No. WO2016/197127.
142. Wang et al., International Patent Application Publication No. WO2017/015381.
143. Wang et al., International Patent Application Publication No. WO2017/019782.
144. Wang et al., International Patent Application Publication No. WO2017/048856.
145. Wang et al., International Patent Application No. PCT/US2016/061890.
146. Wang et al., International Patent Application No. PCT/US2017/026322.
147. Wang et al., International Patent Application No. PCT/US2017/018456.
148. Wang et al., International Patent Application No. PCT/US2017/034011.

149. Wang et al., U.S. patent application Ser. No. 15/624,492, filed Jun. 15, 2017.
150. Chen et al., Low-Dose CT Restoration with Deep Neural Network, to appear in the Proceedings of the International Conference on Fully Three-Dimensional Image Reconstruction in Radiology and Nuclear Medicine, Xi'an, Shaanxi, China, June 2017.
151. Shan et al., Enhancing Transferability of Features from Pretrained Deep Neural Networks for Lung Nodule Classification, to appear in the Proceedings of the International Conference on Fully Three-Dimensional Image Reconstruction in Radiology and Nuclear Medicine, Xi'an, Shaanxi, China, June 2017.
152. Gjesteby et al., Reducing Metal Streak Artifacts in CT Images via Deep Learning: Pilot Results, to appear in the Proceedings of the International Conference on Fully Three-Dimensional Image Reconstruction in Radiology and Nuclear Medicine, Xi'an, Shaanxi, China, June 2017.
153. Claus et al., Metal-Artifact Reduction Using Deep-Learning Based Sinogram Completion: Initial Results, to appear in the Proceedings of the International Conference on Fully Three-Dimensional Image Reconstruction in Radiology and Nuclear Medicine, Xi'an, Shaanxi, China, June 2017.
154. Wang et al., Point/Counterpoint—Machine Learning Will Transform Radiology Significantly Within the Next 5 Years, American Association of Physicists in Medicine, 0094-2405/xxxx/0(0)1/xx, 2017.

What is claimed is:

1. A method of reconstructing an image from tomographic data obtained by an imaging process, the method comprising:
    performing at least one algorithm step on a raw data set or an intermediate data set of the tomographic data to obtain a final reconstructed image, wherein performing the at least one algorithm step comprises:
        performing at least one conventional, non-deep-learning algorithm on a raw data of the tomographic data to obtain an intermediate data set of an initial reconstructed image; and
        performing a deep learning algorithm on the intermediate data set to obtain the final reconstructed image.

2. The method according to claim 1, wherein performing at least one algorithm comprises performing a deep learning algorithm directly on the raw data set to obtain the final reconstructed image.

3. The method according to claim 1, wherein the deep learning algorithm is performed by a deep network.

4. The method according to claim 3, wherein the deep network is a deep neural network, and further comprising training the deep network with a training set of final images, prior to performing the deep learning algorithm.

5. The method according to claim 4, wherein training the deep network comprises performing on the deep network: at least one fine-tuning technique, at least one feature selection technique, or both.

6. The method according to claim 1, wherein the deep learning algorithm is performed by a convolutional neural network (CNN).

7. The method according to claim 1, wherein raw data is obtained by computed tomography (CT), magnetic resonance imaging (MRI), single-photon emission computed tomography (SPECT), or positron emission tomography (PET).

8. The method according to claim 1, wherein performing at least one algorithm comprises performing a deep learning algorithm to complete a sinogram based on the tomographic data.

9. The method according to claim 1, wherein the raw data includes at least one metal artifact and the reconstructed image includes metal artifact reduction (MAR) compared to the raw data.

10. The method according to claim 1, wherein the deep learning algorithm is performed by a deep neural network, the deep neural network being AlexNet, ResNet, or GoogleNet.

11. The method according to claim 1, wherein the raw data comprises a CT image of one or more lung nodules.

12. The method according to claim 1, wherein the raw data comprises a low-dose CT image.

13. The method according to claim 1, wherein the deep learning algorithm reduces noise of the tomographic data such that the final reconstructed image has less noise than does the tomographic data.

14. The method according to claim 1, wherein the at least one conventional, non-deep-learning algorithm comprises at least one selected from the group of: a normalization-based metal artifact reduction (NMAR) algorithm; a filtered back projection (FBP) algorithm; a model-based image reconstruction (MBIR) algorithm; a block-matching 3D (BM3D) algorithm; a total variation (TV) algorithm; a K-SVD algorithm; and an adaptive-steepest-descent (ASD) projection onto convex sets (POCS) (ASD-POCS) algorithm.

15. A system for reconstructing an image from raw data obtained by a medical imaging process, the system comprising:
    a subsystem for obtaining tomographic imaging data;
    at least one processor; and
    a machine-readable medium, in operable communication with the subsystem for obtaining tomographic imaging data and the at least one processor, having machine-executable instructions stored thereon that, when executed by the at least one processor, perform at least one algorithm step on a raw data set or an intermediate data set of the tomographic data to obtain a final reconstructed image;
    wherein the at least one algorithm step comprises:
        performing at least one conventional, non-deep-learning algorithm on a raw data of the tomographic data to obtain an intermediate data set of an initial reconstructed image; and
        performing a deep learning algorithm on the intermediate data set to obtain the final reconstructed image.

16. The system according to claim 15, wherein the deep learning algorithm is performed by a deep network.

17. The system according to claim 16, wherein the deep network is a deep neural network, and further comprising training the deep network with a training set of final images, prior to performing the deep learning algorithm.

18. The system according to claim 17, wherein training the deep network comprises performing on the deep network: at least one fine-tuning technique, at least one feature selection technique, or both.

19. The system according to claim 15, wherein the deep learning algorithm is performed by a convolutional neural network (CNN).

20. The system according to claim 15, wherein the at least one conventional, non-deep-learning algorithm comprises at least one selected from the group of: a normalization-based metal artifact reduction (NMAR) algorithm; a filtered back projection (FBP) algorithm; a model-based image reconstruction (MBIR) algorithm; a block-matching 3D (BM3D) algorithm; a total variation (TV) algorithm; a K-SVD algorithm; and an adaptive-steepest-descent (ASD) projection onto convex sets (POCS) (ASD-POCS) algorithm.

* * * * *